United States Patent
Feher et al.

(10) Patent No.: US 10,337,975 B2
(45) Date of Patent: Jul. 2, 2019

(54) METHOD AND SYSTEM FOR CHARACTERIZING PARTICLES USING A FLOW CYTOMETER

(71) Applicants: Deutsches Rheuma-Forschungszentrum Berlin, Berlin (DE); A•P•E Angewandte Physik & Elektronik GmbH, Berlin (DE)

(72) Inventors: Kristen Feher, Berlin (DE); Toralf Kaiser, Birkenwerder (DE); Konrad von Volkmann, Berlin (DE); Sebastian Wolf, Berlin (DE)

(73) Assignees: Deutsches Rheuma-Forschungszentrum Berlin, Berlin (DE); A•P•E Angewandte Physik & Elektronik GmbH, Berlin (DE)

( * ) Notice: Subject to any disclaimer, the term of this patent is extended or adjusted under 35 U.S.C. 154(b) by 0 days.

(21) Appl. No.: 15/588,155

(22) Filed: May 5, 2017

(65) Prior Publication Data
US 2017/0322137 A1 Nov. 9, 2017

(30) Foreign Application Priority Data

May 6, 2016 (EP) .................................... 16168576
Aug. 15, 2016 (EP) .................................... 16184174

(51) Int. Cl.
*G01N 15/10* (2006.01)
*G01N 15/14* (2006.01)

(52) U.S. Cl.
CPC ..... *G01N 15/1012* (2013.01); *G01N 15/1429* (2013.01); *G01N 2015/1006* (2013.01);
(Continued)

(58) Field of Classification Search
CPC .......... G01N 15/1012; G01N 15/1429; G01N 2015/149; G01N 15/14; G01N 15/1404;
(Continued)

(56) References Cited

U.S. PATENT DOCUMENTS 5,548,395 A * 8/1996 Kosaka ................ G01N 15/147 356/39
9,632,030 B1 * 4/2017 Houston ............ G01N 15/1459
(Continued)

FOREIGN PATENT DOCUMENTS

EP 1865303 A1 12/2007
WO WO 2016/022276 A1 2/2016

OTHER PUBLICATIONS

Brosman K. et al. 2015 "Analysis flow cytometry data using wavelets (cytowave)" significantstats/cytowave index package. (in 1 page).
(Continued)

*Primary Examiner* — Tri T Ton
(74) *Attorney, Agent, or Firm* — Knobbe, Martens, Olson & Bear LLP

(57) ABSTRACT

The invention relates to a method and system for characterizing particles using a flow cytometer comprising generating a waveform, as a digital representation of detected radiated light, and transforming said waveform using one or more basis functions and obtaining one or more coefficients characterizing the waveform. The one or more coefficients characterizing the waveform preferably correspond to particular properties of the particle(s), thereby enabling analysis of physical properties of the particles (such as size or shape) or biological properties of the particles, such as cell type, localization and/or distribution of molecules within the cell and/or on the cell surface, structural elements of the cell such as the nucleus or the cytoskeleton, antibody or antibody-fragment binding to the cell or cell morphology. Pre-
(Continued)

ferred embodiments of the invention relate to methods and systems in which the waveform is transformed by a wavelet transformation or Fourier transformation.

18 Claims, 25 Drawing Sheets

(52) U.S. Cl.
CPC ............... *G01N 2015/1402* (2013.01); *G01N 2015/149* (2013.01)

(58) Field of Classification Search
CPC ....... G01N 15/1459; G01N 2015/1461; G01N 2015/1486; G01P 3/36
USPC .................................................. 356/335–338
See application file for complete search history.

(56) References Cited

U.S. PATENT DOCUMENTS

2013/0016335 A1* 1/2013 Lo ........................... G01P 5/001 356/28
2017/0227466 A1* 8/2017 Lo ....................... G01N 21/6486

OTHER PUBLICATIONS

Damm et al., 2009 "Cell counting for in vivo flow cytometer signals using wavelet-based dynamic peak picking" 2nd international conference on biomedical engineering and informatics, BMEI 2009 (in four pages).

Evander at al., 2013 "Microfluidic impedance cytometer for platelet analysis" Lab on a Chip, vol. 13: 722, 2012.

Extended European Search Report in corresponding European Application No. EP 16 18 4174, dated Apr. 26, 2017.

Galbraith D. et al., 2001 "Wavelet analysis of flow cytometric information" (retrieved from the internet at grantome.com/grant/NIH/R21-CA08).

Galbraith D. et al., 2001 Wavelet analysis of flow cytometric information—University of Arizona onthe internet at: arizona.pure.elsevier.com/en/projects/wavelet-analysis-of-flow-cytometric-information.

Jagtiani et al., 2008 "Wavelet transform-based methods for denoising of coulter counter signals", Measurement Science and Technology, vol. 19 (in 16 pages).

Dubelaar, G.B.J. and Gerritzen, P.L. 2000 "CytoBuoy: a step forward towards using flow cytometry in operational oceanography" *Scientia Marina* 64(2): 255-265.

* cited by examiner

METHOD AND SYSTEM FOR CHARACTERIZING PARTICLES USING A FLOW CYTOMETER The invention relates to a method and system for characterizing particles using a flow cytometer comprising generating a waveform, as a digital representation of detected radiated light, and transforming said waveform using one or more basis functions and obtaining one or more coefficients characterizing the waveform. The one or more coefficients characterizing the waveform preferably correspond to particular properties of the particle(s), thereby enabling analysis of physical properties of the particles (such as size or shape) or biological properties of the particles, such as cell type, localization and/or distribution of molecules within the cell and/or on the cell surface, structural elements of the cell such as the nucleus or the cytoskeleton, antibody or antibody-fragment binding to the cell or cell morphology. Preferred embodiments of the invention relate to methods and systems in which the waveform is transformed by a wavelet transformation or Fourier transformation.

BACKGROUND OF THE INVENTION

Flow cytometry involves the analysis of optical signals produced by suspensions of particles or biological cells passing in a fluid stream through a focused beam of light. The optical signals, derived from radiated light, for example from emission of fluorescence or from light scatter, are converted into voltage-versus-time pulse waveforms through the operation of a detector, such as photodiode or photomultiplier detectors.

Flow cytometry allows simultaneous multi-parametric analysis of the physical and biological characteristics of up to thousands of particles per second. Flow cytometry is routinely used in basic research, to interrogate populations of biological cells that may show cell type or gene/protein expression heterogeneity, in the diagnosis of medical conditions and has many other applications in research and clinical practice. A common application is to physically sort particles based on their properties, so as to purify populations of interest, such as in fluorescence-activated cell sorting (FACS).

Despite significant advances in flow cytometry analysis, established procedures fail to make effective use of the huge amount of data obtained for any given sample, or for any given particle, being analyzed in the cytometric device. For example, typical flow cytometry techniques employ thresholds in order to reduce background noise from the analysis. This is commonly done by designating a parameter as the trigger and setting a level in that parameter as the threshold. Any pulse that fails to exceed the threshold level is ignored in all detectors; any pulse that surpasses the threshold level is processed by the electronics. Typically the pulse height and in some cases pulse width across a trigger window (pulse time) are recorded.

Analyses of this kind however fail to interrogate more complex aspects of the data obtained by the detector, for example the exact shape of the waveform is not interrogated in detail, thereby potential cell doublets, where two cells are fused together, may not be identified. Cells associated with debris are not differentiated, and potentially valuable information on cell shape is lost.

Some improvements have been made in this respect, such as in the methods described in EP 1865303 and WO 2016/022276. These methods enable the detection of characteristic parameters of the cells, or of multi-peak signals, based on waveform analysis. However, the detection and determination of such waveform characteristics is typically carried out based on the height and width of the waveform, with or without some approximation of waveform, thereby discarding detailed information on the particular shape of the waveform as detected.

Moreover it has been proposed in the prior art to use wavelet-denoising algorithms to smooth the raw stream of data in order to improve the identification of peaks. Denoising or smoothing algorithms based upon a wavelet transformation have been proposed e.g. in Evander et al. for a microfluidic impedance cytometer or in Jagtiani et al. for an improved analysis of Coulter counter signals (Evander at al., Lab Chip, vol. 13, p. 722, 2012, Jagtiani et al., Measurement Science and Technology, Vol. 19 p. 065102, 2008). A wavelet-based dynamic peak picking has also been described in Damm et al. to achieve a more accurate cell counting in an in vivo flow cell cytometer (Damm et al. $2^{nd}$ international conference on biomedical engineering and informateics, BMEI 2009). While the smoothing and denoising of the raw data allows for an improved peak detection and cell counting, detailed information on the particular shapes of the peaks are discarded.

In light of the prior art, there remains a significant need to provide additional means for effective processing of flow cytometer data, achieving improvements in identifying and/or characterizing the properties of the particles subject to analysis.

SUMMARY OF THE INVENTION

In light of the prior art the technical problem underlying the present invention is to provide alternative and/or improved means for characterizing particles in a flow cytometer.

This problem is solved by the features of the independent claims. Preferred embodiments of the present invention are provided by the dependent claims.

The invention relates to a method and system for characterizing particles using a flow cytometer comprising generating a waveform, as a digital representation of detected radiated light, and transforming said waveform using one or more basis functions and obtaining one or more coefficients characterizing the waveform.

The invention therefore relates to a method for characterizing particles using a flow cytometer comprising:
 a) passing of one or more particles in a fluid stream through a light beam of the flow cytometer,
 b) detecting radiated light as one or more particles pass through the light beam,
 c) generating a waveform, which is a digital representation of the detected radiated light, and
 d) transforming said waveform using one or more basis functions and obtaining one or more coefficients characterizing the waveform.

The method is preferably characterized in that the one or more coefficients characterizing the waveform correspond to particular properties of the particle(s), thereby enabling analysis of physical properties of the particles (such as size or shape) or biological properties, in particular when the particles are biological cells, or other properties of the particles. In the meaning of the invention, a coefficient that characterizes a waveform corresponding to particular properties of the particle(s) preferably employs using control and/or calibration samples for particular particle populations to be detected, for example for doublets, debris, cell types, or desired cell populations. By obtaining coefficients for particular control and/or calibration particles, the subsequent analysis enables comparison between coefficients of controls and measured samples, enabling particle characterization.

In a preferred embodiment of the method described above, the method is characterized in that the one or more coefficients characterizing the waveform are used for assigning a physical and/or biological property (such as but not limited to size, shape, cell type, morphology, granularity, internal structure) to the one or more particles. Such an assignment is typically not evident in de-noising approaches based on wavelet transformations.

In a preferred embodiment the detected radiated light of the one or more particles is a forward scatter signal (FSC) and the one or more coefficients characterizing the waveform correspond to the shape or morphology of the particles, in particular when the particles are biological cells. In another preferred embodiment the detected radiated light of the one or more particles is a side scatter signal and the one or more coefficients characterizing the waveform correspond to the internal structure or granularity of the particles, in particular when the particles are biological cells.

The methods reported in the prior art that are suitable for application in flow cytometer systems, such as the methods of EP 1865303 and WO 2016/022276, employ analyzing a waveform of the output scattered light measured in a flow cytometer, wherein characteristic parameters are calculated, wherein such parameters are typically selected from the width or height of the peak, or various relationships between width and peak value, such as width/peak value. Alternatively, the methods of the prior art encompass determination of multi-peak signals, whereby a waveform is analyzed to determine whether a potential doublet has been detected. From these measurements conclusions may be drawn regarding particular properties of the cells analyzed in the cytometer.

At present, no mention has been made in the relevant art of using a mathematical transformation of the waveform using a basis function, and obtaining coefficients that characterize the waveform. As preferred examples of methods of transformation, which use one or more basis functions and allow the provision of one or more coefficients characterizing a waveform, wavelet transformation or Fourier transformation are employed. These examples are preferred embodiments that are not limiting to the methods and systems of the present invention.

The Fourier and wavelet transformations are unified by common functional principles. Typically, signal processing in any given application transforms a time-domain signal into another domain, with the purpose of extracting the characteristic information embedded within the time series that is otherwise not readily available in its original form. Mathematically, this can be achieved by representing the time-domain signal as a series of coefficients, based on a comparison between the signal and a set of known template or basis functions (Wavelets, Theory and Applications for Manufacturing; Gao and Yan, 2011, XIV, p 224; Springer). Both Fourier and Wavelet transformations fall into this category of mathematical transformations useful in analysis of signal processing.

Through the application of these mathematical techniques in assessing the waveform of the analyzed particles, significant improvements are achieved compared to earlier systems. The present invention enables interrogation of more detailed characteristics of the particles due to the analysis of a very close approximation of the actual waveform, as represented by the coefficients of the basis function. Where systems of the prior art have significantly reduced the analyzed data to waveform peak height, width, skew, kurtosis, slope, waviness or multi-peak forms, the present invention enables characterization of every analyzed waveform with a high degree of accuracy. The coefficients of the present invention, when combined with the basis function, provide a very accurate description of the true wave form, without needing to record and store all data points obtained from the detector. The present invention therefore enables a fast and efficient computer processing of the data derived by the detector. By dealing with waveform abstractions based on the mathematical transformations described herein, the invention enables the processing and assessment of coefficients of basis functions in order to obtain detailed representation of waveform, without having to deal with unmanageable amounts of raw data, as would be required if the shape of the waveform itself was directly analyzed, as obtained from the detector.

Moreover by obtaining a set of coefficients that characterize the waveforms the properties of the corresponding particles may be deduced without the need for an input of prior knowledge. The method thus allows to generate a novel set of parameters, i.e. a full set of wavelet coefficients or a reduced set of PCA coefficients, which can be used for the discovery of novel particle characteristics. For example in case of biological cells, it could be that a classically defined cell subset differs between two conditions with respect to a subtle shift in a wavelet-derived parameter for which there is no prior biological explanation. By determining the wavelet coefficients even such subtle shifts within a single classically defined population can be detected with respect to the experimental conditions. The method may therefore aid biological discovery. It is particular advantageous that to this end there is no need for prior knowledge as e.g. in form of a library for waveforms of previously known cell types. Instead properties defining subtle differences in cells types can be revealed without additional input.

In one embodiment of the invention the method of the present invention is therefore characterized in that the waveform is transformed by a wavelet transformation. In one embodiment of the invention the wavelet transformation is a discrete wavelet transformation, a continuous wavelet transformation, a single level wavelet transformation, a multilevel wavelet transform or combinations thereof.

A wavelet is a wave-like oscillation with an amplitude, such that the area under the curve (equivalently the definite integral) is zero and must decay rapidly (i.e. it is localized). Generally, wavelets are created to have specific properties that make them useful for signal processing. As a mathematical tool, wavelets can be used to extract information from many different kinds of data, such as audio or light signals and images.

Wavelet transforms, or wavelet transformations, similar to Fourier transforms, can be considered as rotations of data in function space to a different domain. In the new domain the information content of the data can often be extracted with fewer and/or simpler mathematical treatments. For the Fourier transform the new domain is reached by projecting signals onto basis functions that are sine and cosine functions. For the wavelet transform, it can be reached by projecting onto an infinite number of possible basis function sets called wavelets. These wavelet basis functions meet certain mathematical criteria. They can be chosen from known sets or designed by the user to suit the particular application. While Fourier transforms could also be applied to the measured pulses with some degree of success, Fourier analysis is generally more suited to signals that extend in time and have a periodic component. Given that the pulse is measured in a specific trigger window, and the cell-related high frequency component is not periodic within the trigger window, the information can be considered as localized and thus particularly suited to wavelet analysis.

One skilled in the art will know the basis functions of different wavelet transformations. Examples of wavelet transformations may be selected appropriately by a skilled person (see Wavelets, Theory and Applications for Manufacturing; Gao and Yan, 2011, XIV, p 224; Springer; Gilbert Strang and Truong Nguyen, Wavelets and Filter Banks, Wellesley-Cambridge Press, 1996; Amara Graps, "An Introduction to Wavelets," IEEE Computational Science and Engineering, Summer 1995, Vol. 2, No. 2; Wavelet Methods in Statistics with R' by Guy Nason, Springer, Use R! Series).

For x (a real number), let $\Psi(x)$ denote a suitable 'mother wavelet'. Wavelets can then be generated by dilation and translation such that:

$$\psi_{jk} = 2^{\frac{j}{2}}\psi(2^j x - k)$$

If f (x) is the function to be decomposed, the wavelet coefficients are found by $$d_{jk} = \int_{-\infty}^{\infty} f(x)\psi_{jk}(x)dx.$$

Thus the transform is evaluated at different locations (translation) and different scales (dilation). This is the continuous form that could be evaluated at an infinite number of locations and scales. For a discrete sequence, this form could also be used (by evaluating at every discrete location and an infinite choice of scales). However it is more computationally efficient as well as parsimonious to use the decimated discrete wavelet transformation which is evaluated at select scales (without loss of information) in near linear time. The low computational complexity makes it ideal for implementation in hardware. The undecimated discrete wavelet transformation as well as wavelet packet transformations (both decimated and undecimated) could also be used.

In one embodiment of the invention the method described herein is characterized in that the basis function of the discrete wavelet transformation is selected from Haar wavelets or Daubechies wavelets.

Preferred but non-limiting examples of wavelet transform are the dwt and wavedec commands of Matlab, a mathematics and computing platform provided by Mathworks. For example, the dwt command performs a single-level one-dimensional wavelet decomposition. The decomposition is done with respect to either a particular wavelet ('wname') or particular wavelet decomposition filters that can be specified accordingly. [cA,cD]=dwt(X,'wname') computes the approximation coefficients vector cA and detail coefficients vector cD, obtained by a wavelet decomposition of the vector X. The string 'wname' contains the wavelet name.

Alternatively, the wavedec command performs a multi-level one-dimensional wavelet analysis using either a specific wavelet ('wname') or a specific wavelet decomposition filters. [C,L]=wavedec(X,N,'wname') returns the wavelet decomposition of the signal X at level N, using 'wname'. N must be a positive integer. The output decomposition structure contains the wavelet decomposition vector C and the bookkeeping vector L.

In one embodiment of the invention the method the method described herein is characterized in that the waveform is transformed using a Fourier transformation preferably selected from a group comprising discrete Fourier transform, fast Fourier Transforms, short-time Fourier transforms or any combination thereof.

The Fourier transform is one of the most widely used applied signal processing tools in science and engineering. A skilled person is therefore capable of identifying appropriate transforms and software, using the Fourier transform in signal processing applications. The Fourier transform reveals the frequency of a time series x(t) by transforming it from the time domain into the frequency domain (Wavelets, Theory and Applications for Manufacturing; Gao and Yan, 2011, XIV, p 224; Springe).

In one embodiment of the invention the method described herein is characterized in that waveform is corrected for the background level prior to the transformation. In a preferred embodiment the correction for the background level is conducted by obtaining the average value for the background detected radiated light, when no particle is present in the light beam, and subtracting said average value from the waveform. This method of correction from background signals is enabled by the mathematical transformations described herein and represents a significant improvement over those methods typically employed in the art. According to this embodiment an arbitrary threshold is not required. Typically, prior art systems had employed an arbitrary threshold by designating a parameter as the trigger and setting a level in that parameter as the threshold. Any pulse that fails to exceed the threshold level is ignored in all detectors; any pulse that surpasses the threshold level is processed by the electronics. Through this method potentially valuable data that may be relevant for the analysis, but lies underneath the arbitrary threshold, is not assessed. Using the present invention this is not necessary. The waveform can be assessed in its entirety using the mathematical transformation with a basis function and corresponding coefficients. Any background signal can be subtracted in order to more exactly determine which background signal is to be excluded from the analysis.

In one embodiment of the invention the method described herein is characterized in that the waveform is normalized, preferably to its maximum value, prior to the wavelet transformation. To this end the values at each time point of the waveform are preferably divided by the maximum value of said waveform yielding normalized waveforms with a maximal value of 1. This allows for a more robust analysis of the shape of the waveforms of different particles as variations due to variations in the total detected intensity of the particles are taken into account. Advantageously the wavelet transformation may in this preferred embodiment capture shape specific features of the waveforms independent of the height of the waveforms and the total intensity, which allows for a more reliable detection and assignment of particle properties.

In one embodiment of the invention the method described herein is characterized in that the waveform is transformed and a set of one or more coefficients characterizing the waveform are obtained, such that based upon the one or more coefficients and the basis function an approximated waveform can be generated.

Preferably the approximation error in such a reconstruction of the waveform, based upon a suitable comparison metric (such as the sum of squared residuals, where 'residual' is the difference between the approximated waveform and the true waveform, evaluated at each measurement), is less than 10% of the total sum of squares, more preferably less than 5%.

In one embodiment of the invention the method described herein is characterized in that the comparison metric relates to the sum of squared residuals, where 'residual' is the difference between the approximated waveform and the true waveform, evaluated at each measurement.

In one embodiment of the invention the method described herein is characterized in that approximation error refers to the ratio of the area under a curve corresponding to the absolute values of the difference between the waveform and the approximated waveform to the area under the waveform.

In one embodiment of the invention the method described herein is characterized in that the waveform is generated from the detected radiated light using a processing unit that comprises an analog-to-digital converter (ADC).

In one embodiment of the invention the method described herein is characterized in that the waveform is transformed using a processing unit comprising a field programmable gate array (FPGA). Field Programmable Gate Arrays (FPGAs) are semiconductor devices that are based around a matrix of configurable logic blocks connected via programmable interconnects. FPGAs can be reprogrammed to desired application or functionality requirements after manufacturing. A skilled person is capable of selecting an ADC and/or FPGA as is necessary for implementing the present invention. The preferred embodiment is particularly useful for real time processing of the waveforms of the particles, since the processing unit may provide coefficients that represent the waveform in an abstracted, but characteristic form without the need of saving the raw PMT data. Instead the coefficients computed may be used directly for a real time processing of the signals, which allow for downstream sorting applications. To this end it may be particularly preferred to implement on the FPGA in addition the computational steps for a subsequent PCA on the wavelet coefficients, in order to perform a gating based upon the results of the PCA.

In one embodiment of the invention the method described herein is characterized in that the method comprises the step of determining at least one property of the particles based upon the one or more coefficients characterizing the waveform. The present invention enables characterization of, without limitation thereto, physical properties of the particles (such as size or shape) or biological properties of the particles, such as cell type, localization and/or distribution of molecules within the cell and/or on the cell surface, structural elements of the cell such as the nucleus or the cytoskeleton, antibody or antibody-fragment binding to the cell or cell morphology.

In one embodiment of the invention the method described herein is characterized in that the particles are calibration samples with at least one known property and the correlation of the one or more coefficients of the waveform of said calibration samples is calculated to generate a calibration matrix. In its most simple form, the calibration matrix may can refer to the assignment that for any given coefficient X with a value between A and B, the particles are then assigned as doublets. Therefore, a coefficient that characterizes a waveform corresponding to particular properties of the particle(s) preferably employs using control and/or calibration samples for particular particle populations to be detected, for example for doublets, debris, cell types, or desired cell populations. By obtaining coefficients for particular control and/or calibration particles, the subsequent analysis enables comparison between coefficients of controls and measured samples, enabling particle characterization.

In one embodiment of the invention the method described herein is characterized in that the coefficients characterizing the waveform are analyzed using a principal component analysis (PCA). Herein it is particularly preferred that clusters of coefficients are identified in the space of the principal components that indicate a common property of the corresponding particles.

The application of a PCA on the coefficients of the waveforms allows for a fast and reliable characterization of the particles. In particular, PCA enables the identification of populations of particles that share a common property. For instance forward scatter signals correlate with the overall morphology of the particles. By applying a PCA on the coefficients of the waveform and determining clusters of the particles in a plot of the principal components, particles with a similar morphology can be identified. To this end it is not necessary to predefine the morphology of the particles, but instead the PCA may reveal distinct populations. In addition, side scatter data may be used in order to identify particles or cells with similar internal structures or granularity.

Moreover the PCA analysis on the coefficients enables a robust and fast gating of particles with common properties. To this end during a calibration experiment a gate representing particles with a common property may be defined. For subsequent experiments the same gate can be reused to identify particles with said property in an unknown mix of particles. Since the application of a wavelet transformation with a subsequent PCA is computationally not intensive, such a gating procedure is particularly advantageous for real time applications e.g. in a cell sorting device.

It is to be understood that while PCA is a particular preferred multivariate statistical model to reduce the dimension of the coefficients characterizing the waveform other multivariate statistical models may also be advantageously applied.

Further properties of the system or particles may be analyzed by the methods described herein, for example technical noise in the system, due to background light detection, or other artefacts, may be assessed by the methods described herein and assessed or specifically excluded for the analysis of the particles of interest.

In one embodiment of the invention the method described herein is characterized in that the particles are selected from a group comprising cells, vesicles, nuclei, microorganisms, preferably algae or bacteria, beads, proteins, nucleic acids, pollen, extracellular vesicles or any combination thereof.

In one embodiment of the invention the method described herein is characterized in that the particles are cells and the determined property of the cells is or is associated with cell type, localization or distribution of molecules within the cell and/or on the cell surface, the amount of debris on the cell, structural elements of the cell such as the nucleus or the cytoskeleton, antibody or antibody-fragment binding to the cell, cell morphology and/or allows for the distinction between single cells or aggregates of multiple cells.

As is demonstrated below in the examples, various cell types can be determined from one another in a cytometer based on the method described herein.

Various biological cells exhibit clearly distinct shapes both in vivo and in vitro. For example, bacteria may be easily characterised by there their morphological features, being typically categorized into spheres (*cocci* (plural) or *coccus* (singular)), rods (*bacilli* (plural) or *bacillus* (singular), and helical (*spirilla* (plural) or *spirillum* (singular). The main arrangements are single cells, diplo-(pairs), staphylo-(clusters), and strepto-(chains). The present invention enables differentiation of various cell shapes based on the transformation mathematics disclosed herein.

Mammalian cells also exhibit different morphological features, and may be accurately characterized using the methods described herein. For example, as described below, erythrocytes were distinguished from other cells. The cells were obtained from mice blood cells, which is a mix of erythrocytes and leukocytes.

Erythrocytes, or red blood cells (RBCs), are the most common type of blood cell and the vertebrate organism's principal means of delivering oxygen (O2) to the body tissues via blood flow through the circulatory system. In humans, mature red blood cells are flexible and oval biconcave disks. They lack a cell nucleus and most organelles, in order to accommodate maximum space for hemoglobin. The present invention has enabled successfully the detection and differentiation of erythrocytes from other cells, without using specific biological markers, based solely on the analysis of pulse waveform from scattered light and subsequent transformation, as described herein.

According to the present invention the radiated light corresponds to, but without limitation thereto, forward-scattered light, side scattered light, back scattered light and/or fluorescent light.

A further aspect of the invention relates to a flow cytometry system comprising:
 a source for a fluid and particles,
 a fluid nozzle configured to generate a fluid stream comprising the particles,
 a light source configured to generate a light beam that illuminates the fluid stream comprising the particles,
 a detector configured to detect the radiated light of the particles, and
 a processing unit configured to generate a waveform based upon the detected radiated light,
wherein the processing unit is configured to transform said waveform using one or more basis functions and obtaining one or more coefficients characterizing the waveform.

A skilled person is capable of implementing the methods as described herein in the form of software and/or hardware into a cytometry device. The processing unit of a cytometry device or system may comprise multiple computer processors, each configured, by using specific software, for the analysis as described herein.

In one embodiment of the invention the flow cytometry system described herein is characterized in that the processing unit comprises an ADC and an FPGA.

In one embodiment of the invention the flow cytometry system described herein is characterized in that the processing unit is configured to transform the waveform according to a method selected from a wavelet transformation, such as a discrete wavelet transformation, a continuous wavelet transformation, a single level wavelet transformation, a multilevel wavelet transform or combinations thereof, or wherein the basis function of the discrete wavelet transformation is selected from Haar wavelets or Daubechies wavelets, or is selected from Fourier transformation, preferably discrete Fourier transform, fast Fourier Transforms, short-time Fourier transforms or any combination thereof. The transforms can be embodied and integrated into a device in the form of an appropriate software, such as using the functions encompassed by the Matlab platform.

In one embodiment of the invention the flow cytometry system described herein is characterized in that the flow cytometry system comprises a sorter for the particles configured to sort the particles based upon the one or more coefficients characterizing the waveform. This application represents an additional function of the invention, for example by combining the methods and systems disclosed herein with a particle/cell sorting device, such as a FACS. The determination of particular coefficients for particular particles may subsequently be coupled with appropriate sorting technology. For example, the system may be configured so that there is a low probability of more than one particle/cell per droplet. Just before the stream breaks into droplets, the flow passes through a measuring station where the property or characteristic of interest of each particle/cell is measured using the methods described herein. An electrical charging ring is positioned at the point where the stream breaks into droplets. A charge is placed on the ring based on the immediately prior measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

A particular advantage of the method described herein is that it allows for a label-free sorting of particles, e.g. cells. Known cell sorting devices such as FACS rely on fluorescent markers. By combining a transformation of the waveform to derive coefficients characterizing the properties of the cells with a subsequent sorting device, a fluorescent labelling of cells is not essential to sort different cell types. Instead forward or side scatter signals of unlabelled cells may be used, wherein a pattern of common coefficients of the waveform indicate a certain cell type. For instance forward scatter predominantly relates to the shape or morphology of cells, while side scatter signals are predominantly influenced by internal structures indicating a degree of granularity. Cell types can be distinguished based upon these properties, however previous methods have not been sufficiently fast to allow for a real time sorting, while being sufficiently precise for a label-free distinction of cell types. For instance, imaging techniques with a subsequent image analysis can precisely identify cell types based on their morphology, but lack speed in order to allow for efficient real time cell sorting applications. On the other hand standard flow cell cytometer parameters such as the width or height of the cells cannot reliable discriminate cells types with more subtle morphological differences.

The transformation of the waveforms of the scatter signals of the cells allow for a fast and surprisingly reliable identification of cell types. In this regard it is particularly preferred to perform a PCA on the coefficients of the waveform for a subsequent gating. Herein, the PCA allows for an identification of cells of a common type, since corresponding waveform coefficients cluster in a plot of the principal components. Known cell types may be used to establish a gate, wherein this gate is subsequently used for real time cell sorting. To this end it may be particularly preferred to implement the transformation of the waveforms as well as the subsequent PCA of the coefficients in a processing unit comprising a field programmable gate array (FPGA). Since both mathematical operations are computationally not intensive, such a hardware implementation enables a real time label-free sorting of cells based upon the overall morphology of the cells (shape) or internal structures (granularity).

DETAILED DESCRIPTION OF THE INVENTION

To provide a more detailed description of the present invention, the following preferred embodiments are discussed below.

With reference to FIG. 35, either fluorescent/stained or unstained cells pass through a laser beam and the respective emitted or scattered light is captured by a light detector (e.g. photo multiplier tube). A current pulse is generated for each event, and the pulse is summarized by its height, area, and width in a standard flow cytometer, with no access to the raw readout of the detectors. The present invention utilizes the shape of the pulse, as it is correlated to the shape of the cell (scattered light) or the surface localization of a biomarker (emitted light). The present invention therefore relates to a method and system that are able to measure the cell specific pulse shape (waveform) based on the detector readout. The shape of the pulse is summarized by coefficients of, preferably, a discrete wavelet transform (or continuous wavelet transform or discrete/continuous Fourier transform). This more comprehensive representation of the waveform compared to previous methods can be used for improved data quality (singlet/doublet discrimination, dead cells, debris) as well as a biological parameter (erythrocytes, discrimination between lymphocytes/granulocytes).

The source of the system is typically the source of the sample that is provided to the flow cytometer for analysis. The sample includes the individual particles that are illuminated by the light beam (from the light source) and analyzed by the detector.

A wide variety of different types of samples can be analyzed by the flow cytometer. Several examples of types of samples include blood, semen, sputum, interstitial fluid, cerebrospinal fluid, cell culture, seawater, and drinking water. The sample may be in the form of a prepared sample, such as lysed blood, labeled particles in suspension, immunoglobulin-labeled cells, or DNA-stained cells, achieved commonly by adding reagents and performing protocols as commonly known in the art.

Examples of types of particles include beads, blood cells, sperm cells, epithelial cells, cancer cells, immune cells, viruses, bacteria, yeast, plankton, microparticles (e.g., from plasma membrane of cells), and mitochondria.

The sample source can include one or more containers, such as test tubes, that hold the sample to be analyzed. A fluid transfer system is provided in some embodiments, such as to aspirate the sample from the container and deliver the sample to the fluid nozzle.

The sample is typically injected into a sheath fluid within the flow cytometer, which is provided by a sheath fluid source. An example of a sheath fluid is saline. An example of the fluid source is a container storing saline therein, and a fluid transfer system operable to deliver the sheath fluid from the fluid source to the fluid nozzle.

In some embodiments a fluid nozzle is provided to generate the fluid stream and to inject the particles of the sample into the fluid stream. An example of a fluid nozzle is a flow cell. The fluid nozzle typically includes an aperture having a size selected to at least be larger than the sizes of particles of interest in the sample, but small enough to arrange the particles into a narrow stream. Ideally the particles are arranged in a single file or near single file arrangement so that a single particle, or a small number of particles (e.g., 1-3), can be passed through the light beam at a time. In some embodiments the particles are focused using hydrodynamic, acoustic, or magnetic forces.

A light source (which can include one or more light sources) generates at least one light beam that is directed toward the fluid stream. Examples of light sources include a laser and an arc lamp. In some embodiments the light beam passes through an optics assembly, such as to focus the light beam onto the fluid stream. In some embodiments the light beam is a laser beam.

The light beam from the light source intersects the fluid stream. The particles contained in the light beam disturb the light beam and generate radiated light. The type and pattern of radiated light depends upon the type and size of the particles, but the radiated light can include forward scattered light, side scattered light, back scattered light, as well as fluorescent light (which occurs when light rays are absorbed and reemitted by the particle, which is detectable by the corresponding change in wavelength (i.e., colour) of the light rays).

One or more detectors are provided to detect radiated light. For example, the detectors may include a detector arranged to detect forward scatter and florescence, a detector arranged to detect side scatter and florescence, and detector arranged to detect back scatter and florescence. One example of a detector is a photomultiplier.

The system of the invention also preferably comprises a processing unit (or particle analyzer) that operates to receive signals from the one or more detectors to perform various operations to characterize the particles. In some embodiments, the processing unit or particle analyzer includes one or more processing devices and a computer-readable storage device that stores data instructions, which when executed by the processing device cause the processing device to perform one or more operations, such as those discussed herein. In some embodiments the system (preferably a particle analyzer) includes an analog to digital converter (ADC), a processing unit comprising a field programmable gate array (FPGA), and/or firmware.

Any time a relevant particle passes through the interrogation point and generates a signal a pulse is generated in every PMT detector. These pulses reflect the passage of the cell through the laser beam and the signal generated at each point in the cell's path. These pulses can be mapped by plotting signal as a function of time, thereby generating a waveform. As the particle enters the laser beam spot, it will generate scattered light and fluorescence signals, which will ultimately manifest in a stream of electrons (current) from the anode of the PMT. The magnitude of the current is proportional to the number of photons that hit the photocathode and thus is also proportional to the intensity of the scatter or fluorescence signal generated by the particle. As the particle enters the laser beam spot, the output of the PMT will begin to rise, reaching peak output when the particle is located in the center of the laser beam. At this point, the particle is fully illuminated (the laser beam's photons are at highest density in the center of the laser beam) and will produce a maximum amount of optical signal. As the particle flows out of the laser beam, the current output of the PMT will drop back to baseline. This generation of a pulse is termed an "event."

As the pulses are generated, their quantification is necessary for signals to be displayed, analyzed, and interpreted. This is conducted by the signal processing electronics.

The majority of flow cytometers and cell sorters are now digital systems, such that cytometers with ADC are suitable for carrying out the present invention. The analog current from the PMT is first digitized or broken down into very small slices by the analog to digital converter (ADC). This process is called "sampling." A sample of a pulse captures the signal at an instant in time and stores it as a digital value. Together these samples represent the entire pulse and optical signal from the particle.

The electronics of systems of the prior art typically quantify the pulse by calculating its height, area, and width. The height and area, or maximum and integral, respectively, are used to measure signal intensity because their magnitudes are proportional to the number of photons that interacted with the PMT. The width, on the other hand, is proportional to the time that the particle spent in the laser and can be used to distinguish doublets (that is, two particles that pass through the laser so closely that the system assigned both of them to a single pulse and event) from singlets. The measurement from each detector is referred to as a parameter. Each parameter can be displayed in height, area, and width values on the histograms and dot plots in flow cytometry software. These are used to measure fluorescence intensity, compare populations, and designate sorting decisions.

According to the present invention, radiated light is detected as one of the one or more particles pass through the light beam, and subsequently a waveform, which is a digital representation of the detected radiated light, is generated, and said waveform is transformed using one or more basis functions and obtaining one or more coefficients characterizing the waveform. The digital signal therefore is a waveform for each event, which is transformed, preferably by a particle analyzer or processing unit, preferably comprising a field programmable gate array (FPGA), according to the mathematical transformations described herein. The electronics of the system therefore provide coefficients that represent the waveform in abstracted form, from which a very accurate representation of the waveform can be constructed, if so desired.

In preferred embodiments of the invention reconstruction of the actual waveform is however unnecessary for analysis. In preferred embodiments the coefficients of an analyzed particle from any given event is compared to a set of control or calibration coefficients, for example in a calibration matrix, in order to characterize the measured particle. In this way, by the use of appropriate calibration samples and the determination of control coefficients for each of the particular artefacts or desired outcomes of the analysis, the method can be conducted in an automated manner based on categorizing the coefficients of each event/pulse.

In some embodiments the coefficients characterizing the waveforms can then be assessed using a multivariate statistical model, such as a principal component analysis. The multivariate statistic model comprises multivariate analysis of variance, multivariate regression analysis, factor analysis, canonical correlation analysis, redundancy analysis, correspondence analysis, multidimensional scaling, discriminant function, linear discriminant analysis, clustering systems, recursive partitioning, principal component analysis, non-linear principal component analysis, information preserving component analysis (IPCA), independent component analysis, multidimensional scaling, support vector machines, random forests, neural networks, partial least squares regression, projection pursuit, boosting and/or artificial neural networks. The principal component analysis can also be termed PCA. The person skilled in the arts knows that PCA is a model of multivariate statistics, which describes a form of statistics encompassing the simultaneous observation and analysis of more than one statistical variable. This analysis enables grouping of the analyzed particles (or their coefficients, as determined by the relevant transform) into sub-populations, such as those associated with particular particle characteristics as described herein.

In some further preferred embodiments machine learning algorithms are used in order to discriminate between at least two populations of particles with a different property based upon the corresponding coefficients characterizing the waveforms. To this end the coefficients characterizing the waveforms are determined for a training set of particles e.g. differing cell types.

On the training data an appropriate Support Vector Machine (SVM) can be constructed and tuned. The SVM may be constructed using the wavelet coefficients from the training set, e.g. an FSC signal, SSC signal or a combination thereof. To obtain an optimized SVM the parameter combination with the highest classification for the training set is chosen. This optimized SVM may be used to reliable discriminate particles in subsequent testing assays.

The invention also comprises the analysis of stored flow cytometry data. The "real-time" analysis of waveforms is preferred, but not essential. Data may also be stored and analyzed subsequently.

FIGURES

The invention is further described by the following figures. These are not intended to limit the scope of the invention, but represent preferred embodiments of aspects of the invention provided for greater illustration of the invention described herein.

EXAMPLES

The invention is further described by the following examples. These are not intended to limit the scope of the invention, but represent preferred embodiments of aspects of the invention provided for greater illustration of the invention described herein.

In standard flow cytometry, cells are characterised by an estimate of scatter and fluorescence intensities. These estimates are derived from an electronic pulse corresponding to the physical response of a detector (PMT or Photo diode), which in turn corresponds to the characteristics of emitted and scattered light from a cell. Usually, the pulse height and width were used to distinguish between single cells and doublets. In the present examples, these pulses are captured and their shapes analyzed using a discrete wavelet transform. The stability of this method is confirmed with the QuantiFlash device (Example 1) as well as with microspheres (Example 2). We are able to efficiently filter out cell doublets and non-specific pulses to increase data quality. Furthermore, we are able to identify erythrocytes which we confirm with a specific erythrocyte staining (Example 3). This method enables the identification of a greater range of cell types, as well implementation in a sorter yielding high purity particle/cell sorts.

Example 1: Quantiflash Response

The Quantiflash calibration device (A.P.E. Angewandte Physik & ELektronik GmbH, Berlin) was used as a model system to assess wavelet transformation of waveform. Quantiflash is a precise LED based light source typically applied in independent quality control and calibration of flow cytometry applications. The Quantiflash generates simulated high-precision pulsed light signals that are collected in a similar manner to the light emitted from a fluorescent cell. Each event creates a pulse. When the pulse rises above a threshold, the device is 'triggered' and a fixed number of digital samples is collected and saved.

Figure 1:
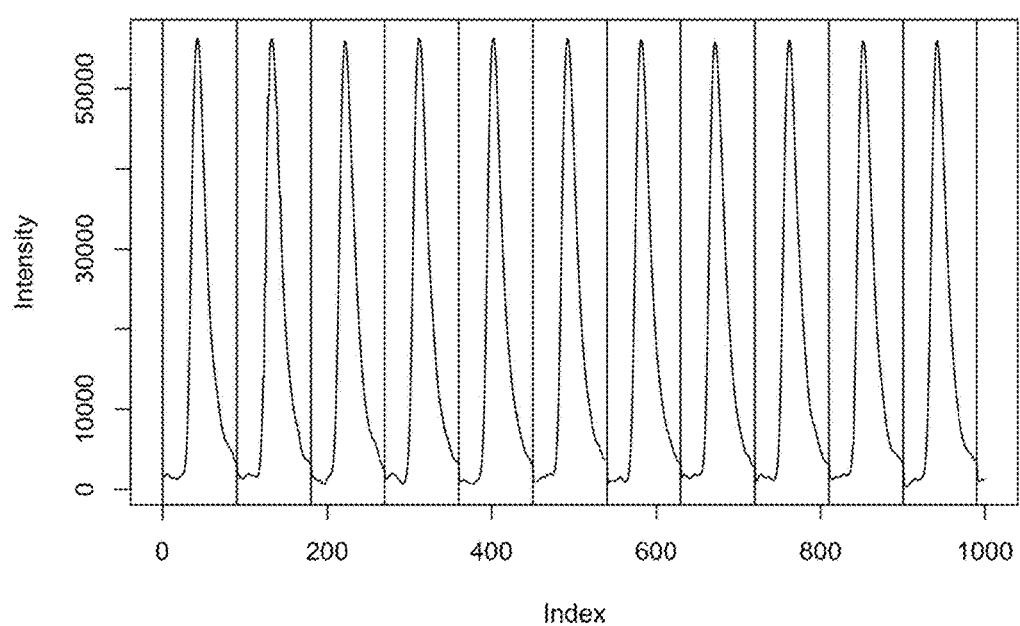
FIG. 1: Pulses generated with the quantiFlash calibration device. The vertical lines indicate the 'trigger window'.

In FIG. 1, pulses are generated with the quantiFlash calibration device, and the vertical lines indicate the 'trigger window'.

A discrete wavelet transform (DWT) was run on each on each trigger window. A DWT function was applied, as used in R, Matlab etc. For reference refer to 'Wavelet Methods in Statistics with R' by Guy Nason (Springer, Use R! Series).

The input for DWT is a vector of length $2^k$, where k is an integer. Here, the trigger window is padded with zeroes on each end, to become length $2^7$.

The output is two sets of coefficients: smoothed coefficients and detail coefficients. Each set of coefficients has k levels. The first level has $2^{k-1}$ coefficients, the second $2^{k-2}$ coefficients etc. The $k^{th}$ level has 1 coefficient. The smooth coefficient of the $k^{th}$ level corresponds to Area, the commonly used parameter.

To summarize the coefficients, the position in the trigger window at which the raw waveform is at its maximum signal was identified. All the coefficients were obtained corresponding to this position. There were k smooth coefficients, and k detail coefficients.

We tested this method using the quantiFlash. This device has been designed to be highly stable, so it should be expected that the coefficients are close to identical. This verifies the stability of the DWT method.

Figure 2:
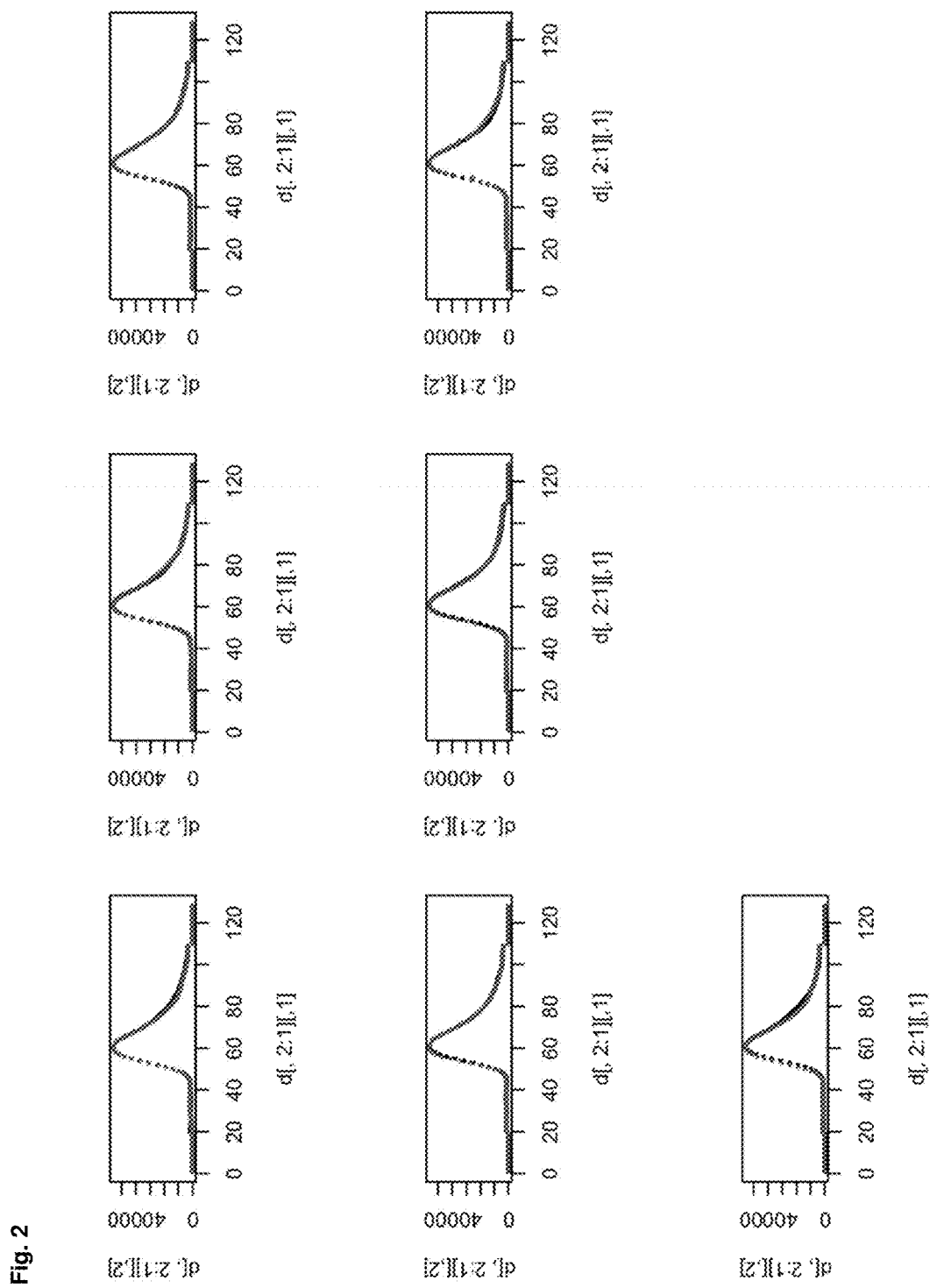
FIG. 2: Correspondence between pulse shape and coefficients.

The shape of the input quantiFlash pulse is programmable, so this could be used to discover the correspondence between pulse shape and coefficients in a robust manner. In FIG. 2 the most extremely different waveforms for each level of the smooth coefficients (plotted in grey and black respectively) are demonstrated. The difference is barely perceptible.

Example 2: 8-Peak Beads

Figure 3:
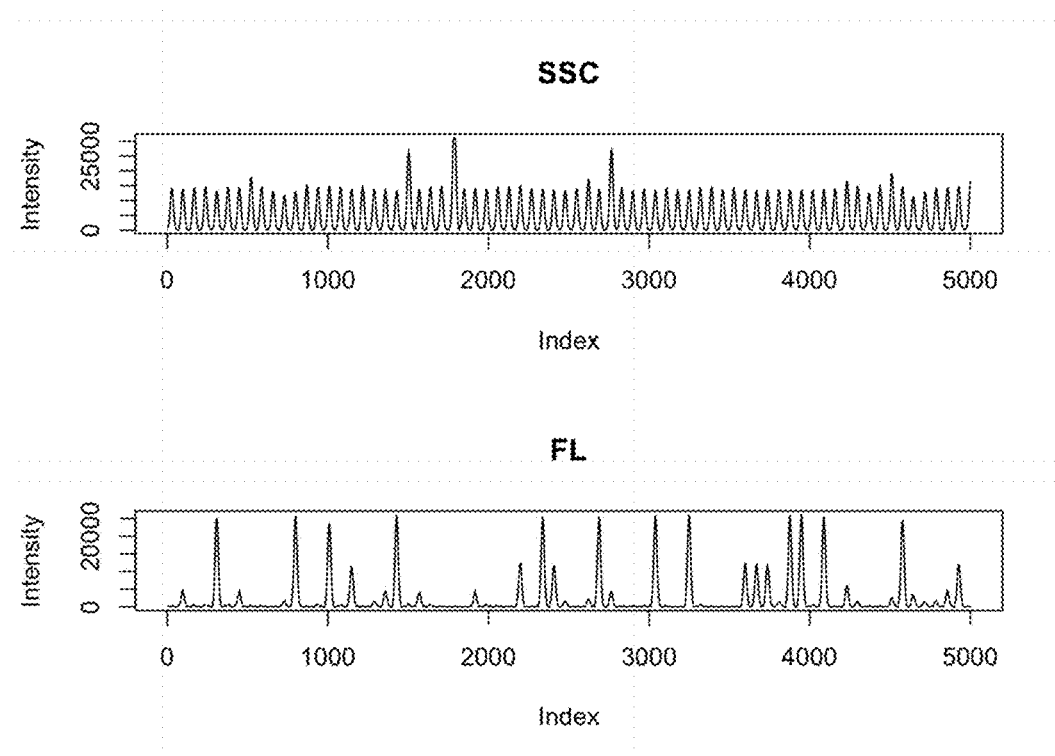
FIG. 3: Raw data from eight-peak beads (beads with 8 fluorescence intensities), from both the side scatter and fluorescence channel.

FIG. 3 shows a plot of raw data from eight-peak beads (beads with 8 fluorescence intensities), from both the side scatter and fluorescence channel. The vertical lines have been omitted. The two streams of data are sychronised, so the peaks are aligned. The intensity is shown on a linear scale, so some fluorescence peaks are very small and not visible.

Figure 4:
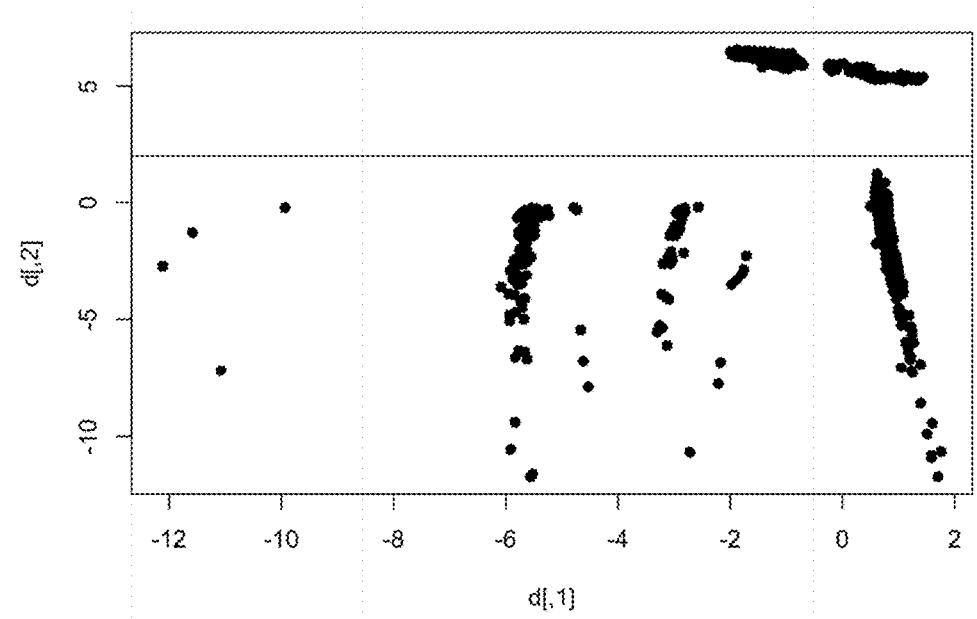
FIG. 4: Analysis of the waveform of the scatter channel.

FIG. 4 demonstrates analysis of the waveform of the scatter channel, and finding the effect on the fluorescence channel, where the signal is. Low quality pulses were first filtered out, then doublets were identified. A principal component analysis (PCA) of the smooth coefficient is displayed.

Figure 5:
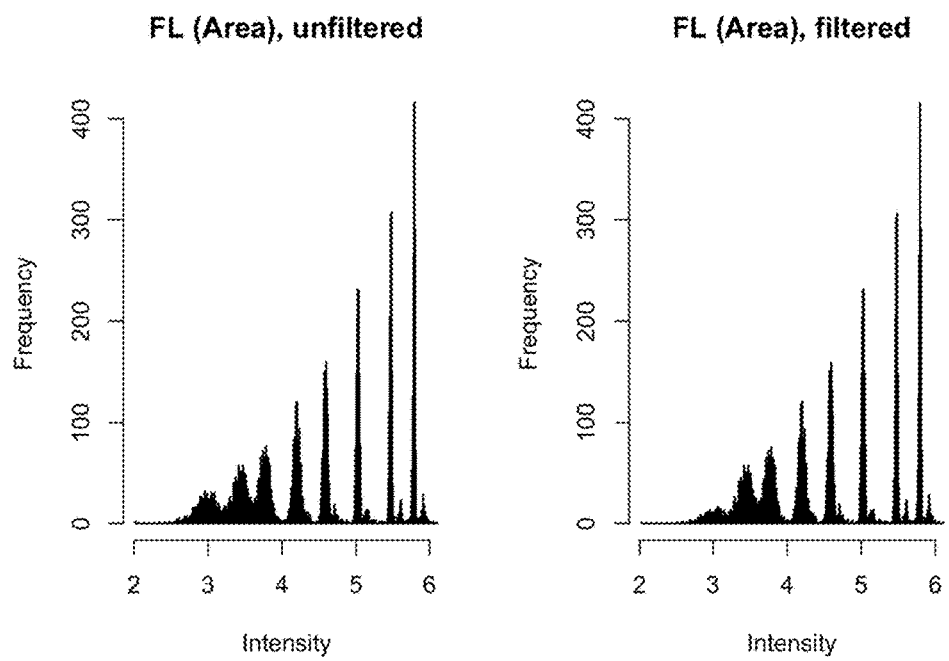
FIG. 5: Histogram of the fluorescent channel, unfiltered (above) and filtered (below).

FIG. 5 demonstrates a histogram of the fluorescent channel, unfiltered (above) and filtered (below). The lowest intensity is mixed with noise, and this has been reduced. Notice that the peaks have a small 'shadow' next to them.

Figure 6:
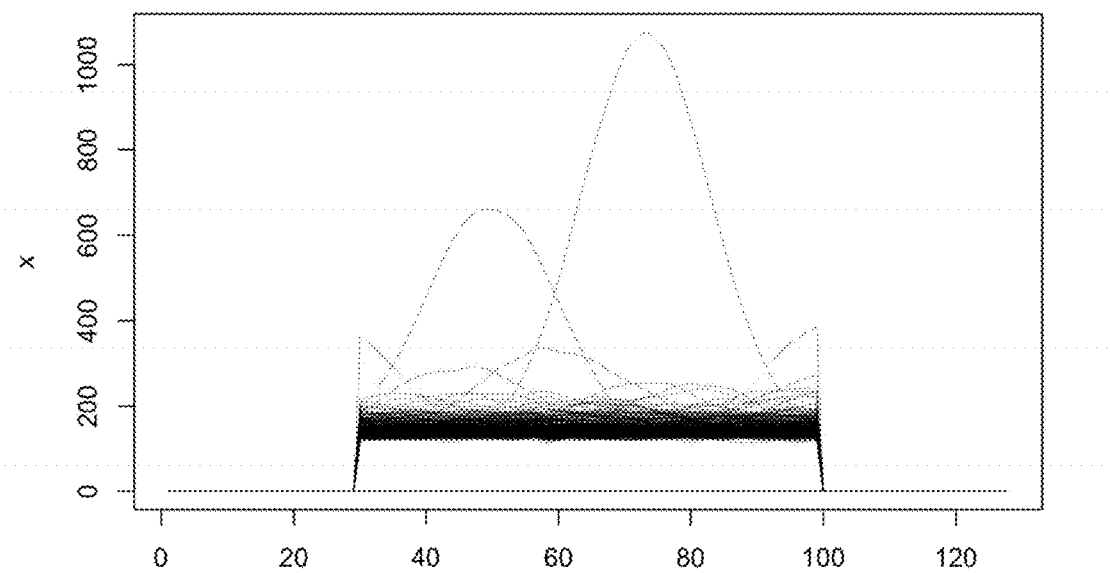
FIG. 6: Low quality waveforms.
Figure 7:
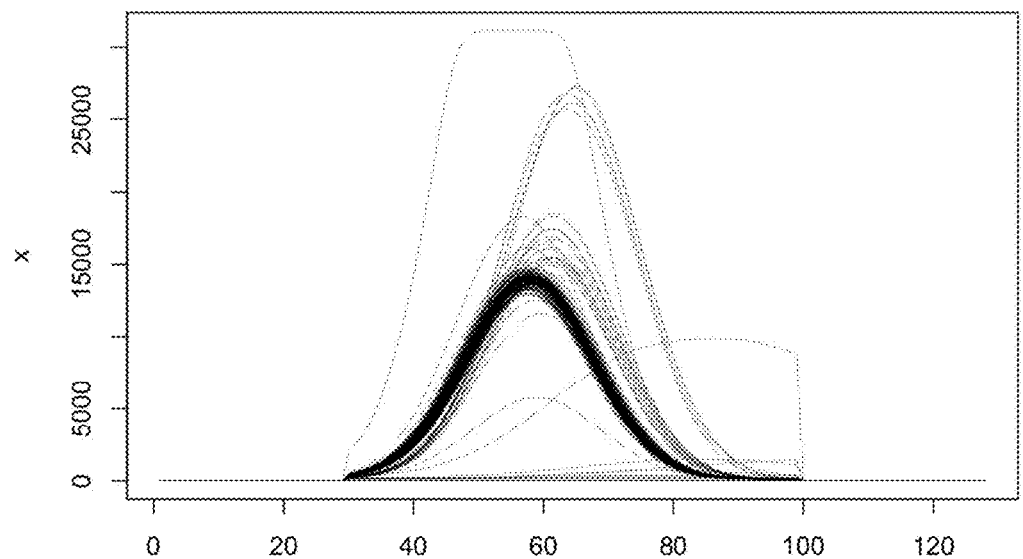
FIG. 7: Filtered waveforms with low fluorescence intensity

In FIG. 7 the filtered waveforms that have low fluorescence intensity are plotted. Note that these waveforms and the waveforms of FIG. 6 have roughly the same energy, but different shapes. Of course, they could also be distinguished by their height differences, but using the DWT eliminates the need for any extra calculations.

Figure 8:
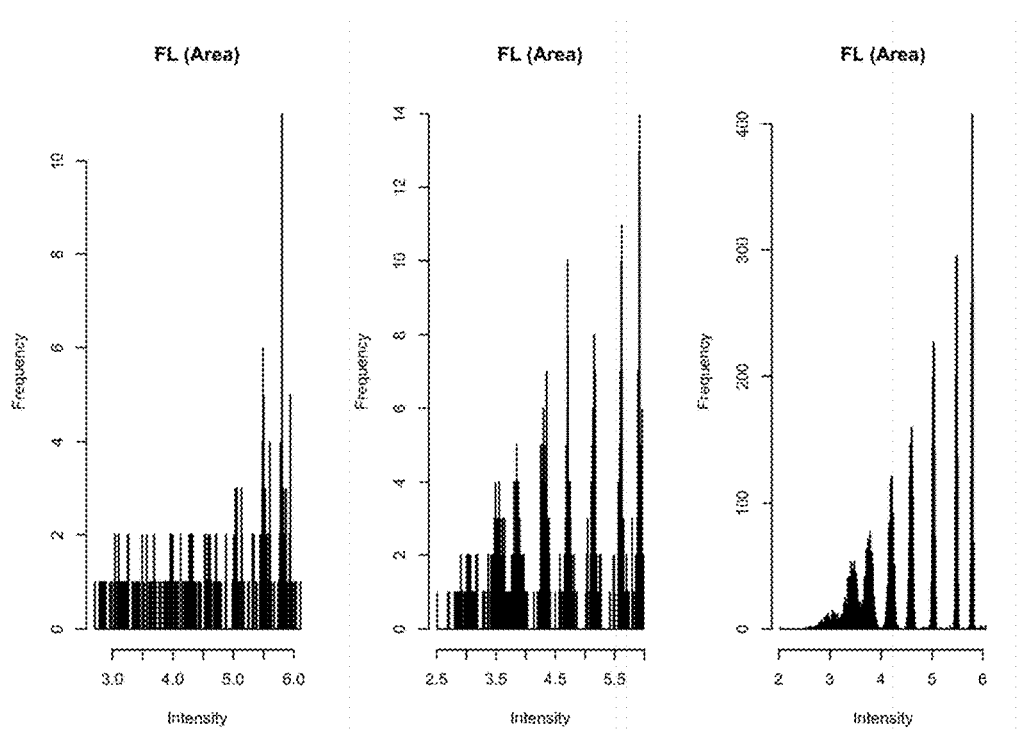
FIG. 8: Three separate components of the filtered events
Figure 9:
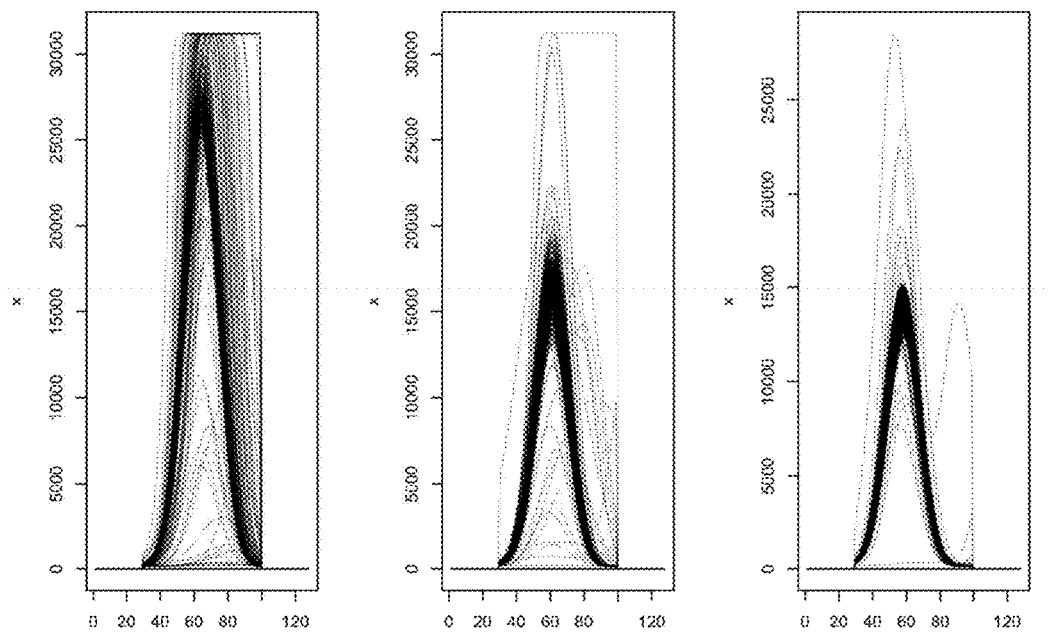
FIG. 9: Corresponding waveforms to the components of FIG. 8.

FIG. 8 shows 3 separate components of the filtered events. By assessing the histograms of the fluorescence intensities, it's possible to separate the main peaks from the 'shadow'. FIG. 9 shows the corresponding waveforms to the components of FIG. 8. This is not necessary for the method or this example, but it's helpful when analyzing cells when there is high overlap in FSC/SSC.

Example 3: Erythrocytes

The analysis of erythrocytes was carried out as follows. First the doublets were identified. The coefficient of the forward scatter was found, and the PCA of the smooth and detail coefficients combined was plotted. Either the smooth coefficients and/or the detail coefficients may be employed. The events on the right of FIG. 10 are the doublets.

Figure 10:
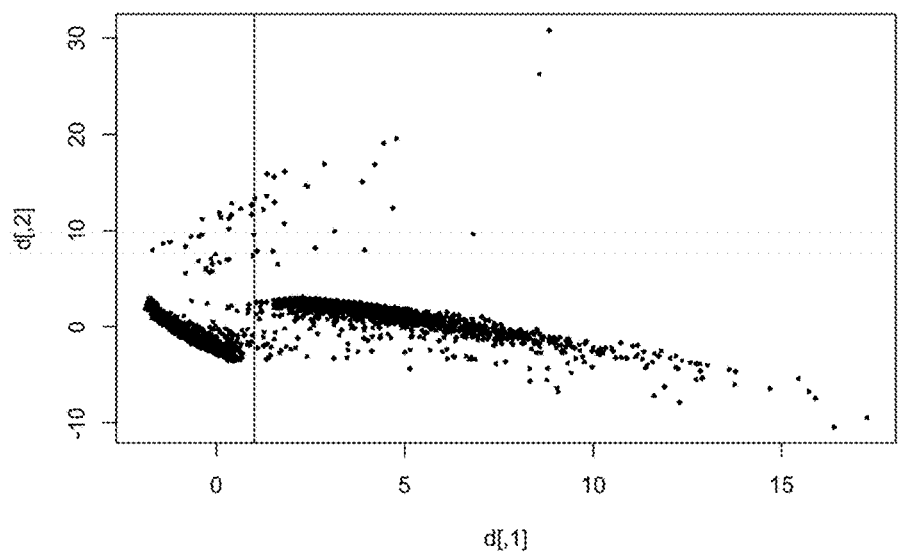
FIG. 10: PCA of the smooth and detail coefficients combined is plotted after analysis or erythrocytes.
Figure 11:
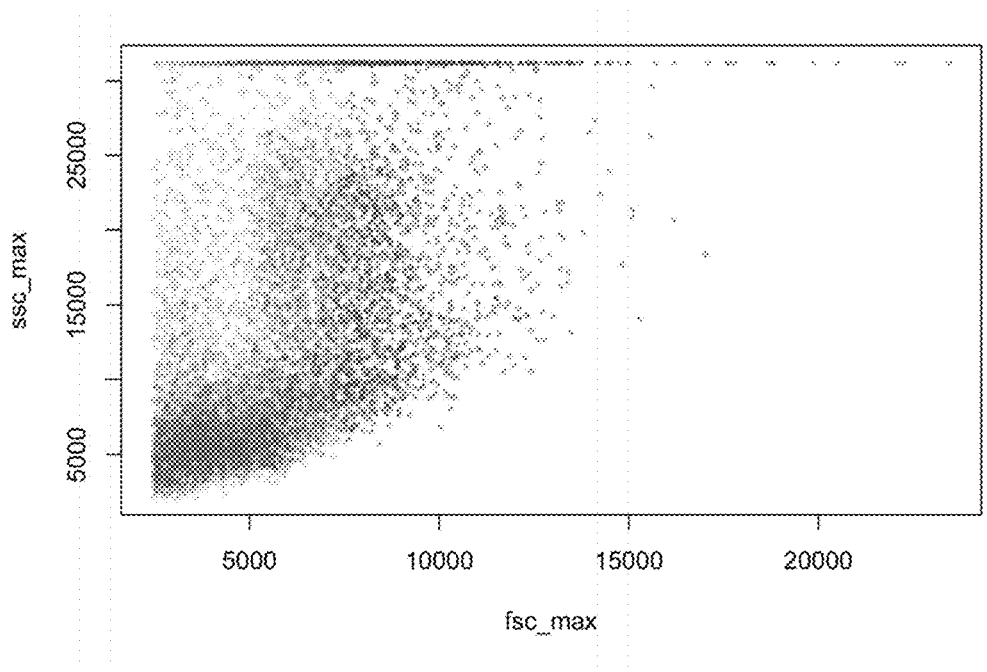
FIG. 11: Standard forward/side scatter dot-plot and identification of doublets (red).
Figure 12:
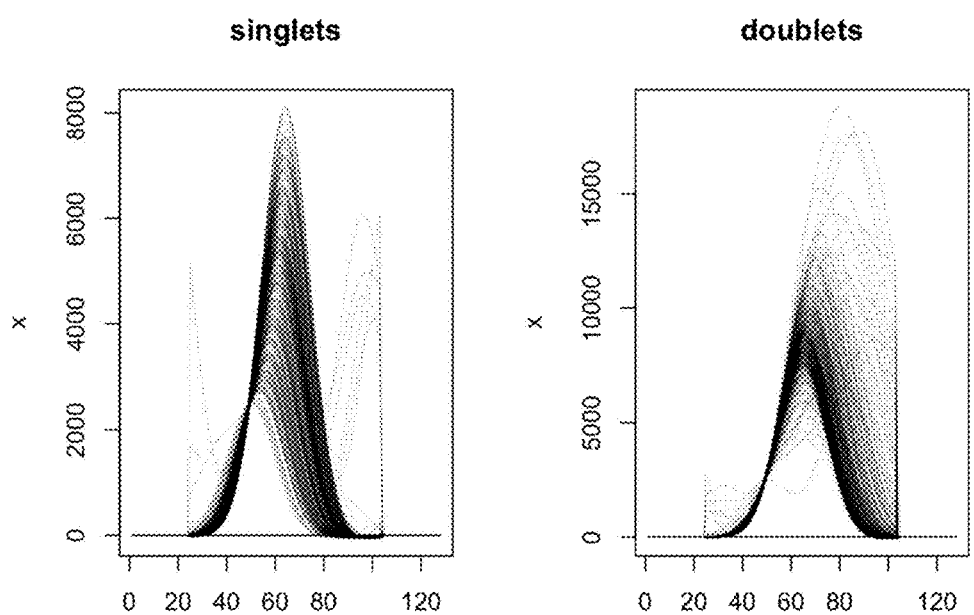
FIG. 12: Waveforms corresponding to singlets/doublets.

The filter shown in FIG. 10 is shown as a standard forward/side scatter dotplot in FIG. 11. The doublets (red) found by the DWT method are in the location that doublets are known to be found in, but they are mixed with singlets, making it impossible to make one single neat gate. The waveforms corresponding to singlets/doublets are shown in FIG. 12.

Figure 13:
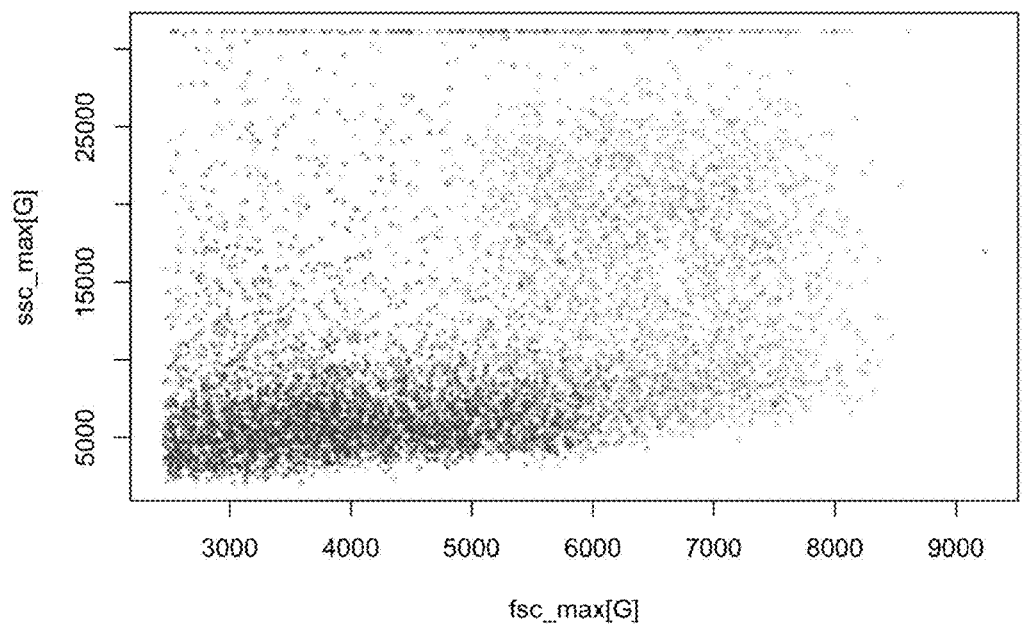
FIG. 13: Erythrocytes plotted in a standard FSC/SSC plot show they are highly overlapping data points with cells.
Figure 14:
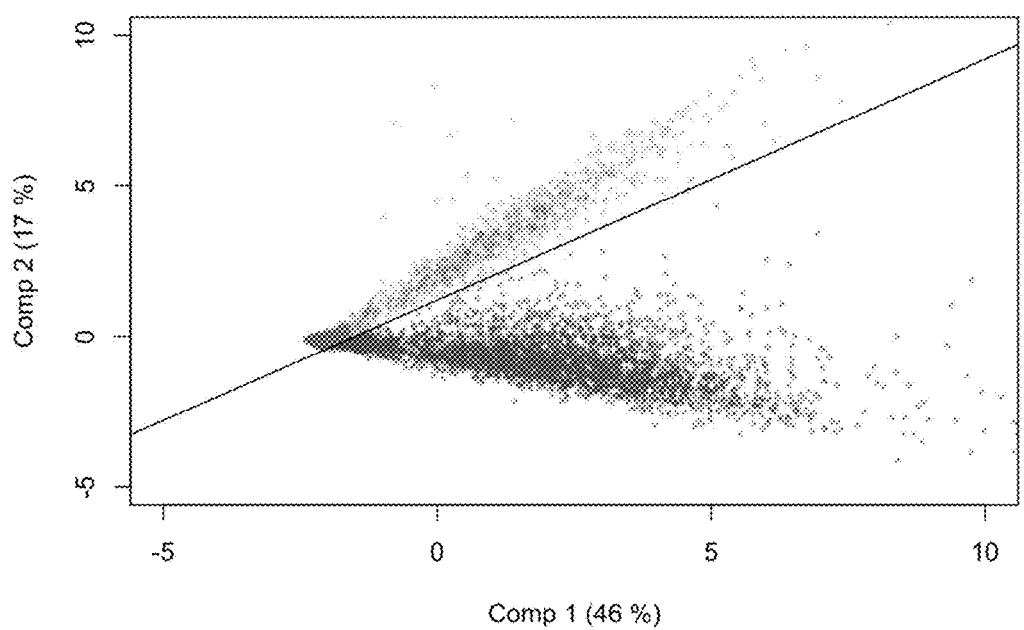
FIG. 14: Plot of wavelet coefficients of cells vs erythrocytes according to their wavelet forms of the relevant fluorescent channel corresponding to the applied marker.

FIG. 13 shows erythrocytes plotted in a standard FSC/SSC plot. They are highly overlapping, which makes it hard/impossible to gate out. However, according to their wavelet forms they are quite distinct (FIG. 14).

Figure 15:
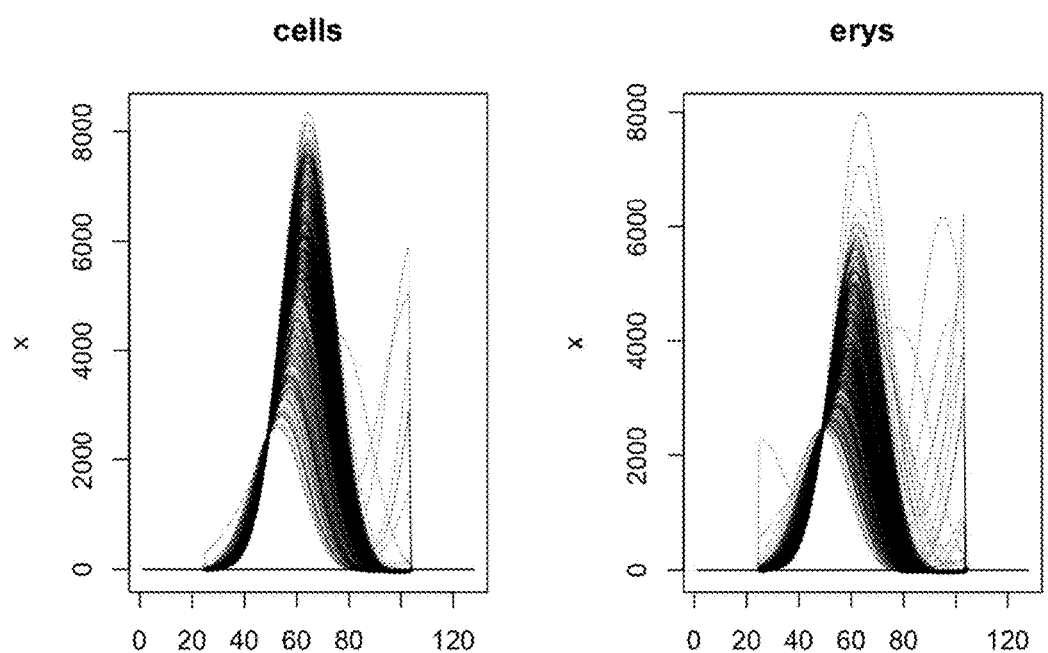
FIG. 15: Plot of waveforms of cells vs erythrocytes.

As can be seen in FIG. 15 from the representation of the waveforms, it's not easy to distinguish the leukocytes from the erythrocytes by eye, highlighting the need for an unbiased mathematical method.

Figure 16:
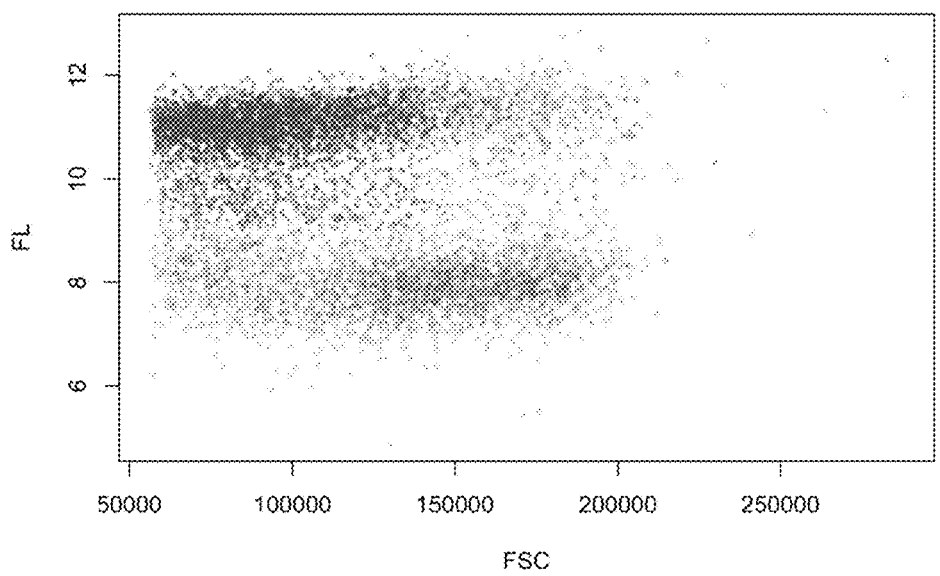
FIG. 16: Fluorescence vs. FSC.

It's also possible to stain the erythrocytes with a fluorescent marker (FITC ter119). FIG. 16 shows a plot of Fluorescence (FITC ter119) vs. FSC to see how this corresponds to the marker. The events (in red are the wavelet coefficients) discovered by the DWT method correspond to the marker. The fluorescent marker also non-specifically stains other lymphocytes meaning erythrocytes cannot be accurately determined in standard methods. When other small particles are of interest (e.g. stroma cells), the erythrocytes cannot be removed from the sample as such procedures also remove these small particles. However it is currently not possible to target erythrocytes with high specificity because in this case, the lymphocytes and erythrocytes are stained with the same marker at the same intensity. However, the fluorescent pulse shapes of the lymphocytes and erythrocytes are different, making a separation possible.

Example 4: Human PBMCs

Furthermore an analysis of human peripheral blood mononuclear cells (PBMCs) stained for CD3, CD4, CD8 and CD14 was conducted.

Figure 17:
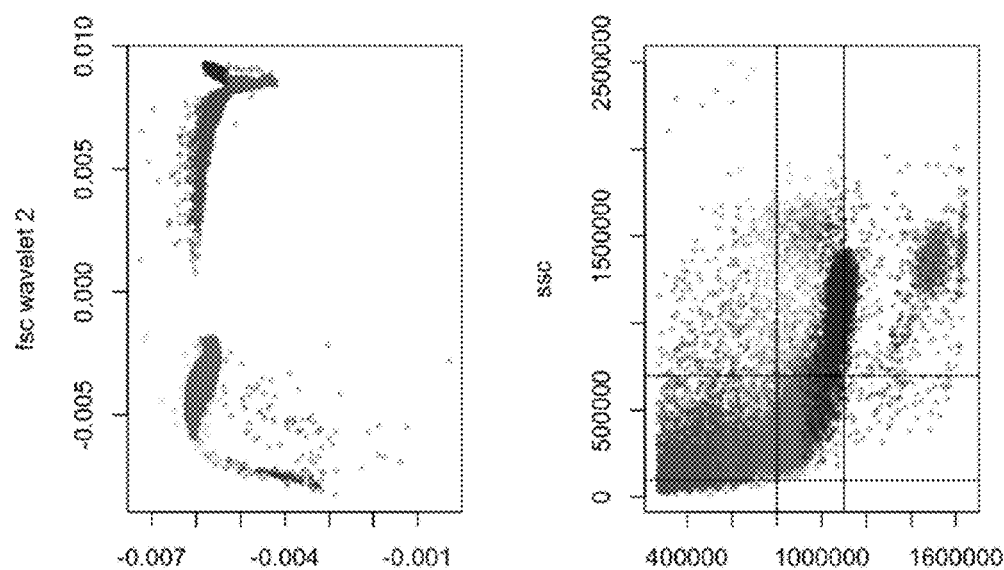
FIG. 17: Comparison of the separation of PBMCs stained for CD3, CD4, CD8 and CD14 in a standard forward scatter/side scatter dot plot versus a plot of the forward-scatter derived wavelet coefficients

The left side plot of FIG. 17 shows a plot of the wavelet coefficients derived from forward scatter. As can be seen the events are well separated into different groups. These groups are overlapping in a standard forward scatter/side scatter plot, which is shown in the right of FIG. 17. In the standard forward scatter/side scatter plot it is thus difficult to accurately identify the different groups.

However by taking advantage of the wavelet analysis shown on the left it is possible to identify debris (red), erythrocytes (pink, bottom left of right figure), lymphocytes and granulocytes (blue). Moreover the black events appear to represent a mixture of lymphocytes and monocytes, suggesting the possibility of distinct types of lymphocytes.

The events are framed in the right figure, with a range of 800000-1100000 in forward scatter (fsc) and 100000-700000 in side scatter (ssc). These framed lymphocytes were analyzed in more detail.

Figure 18:
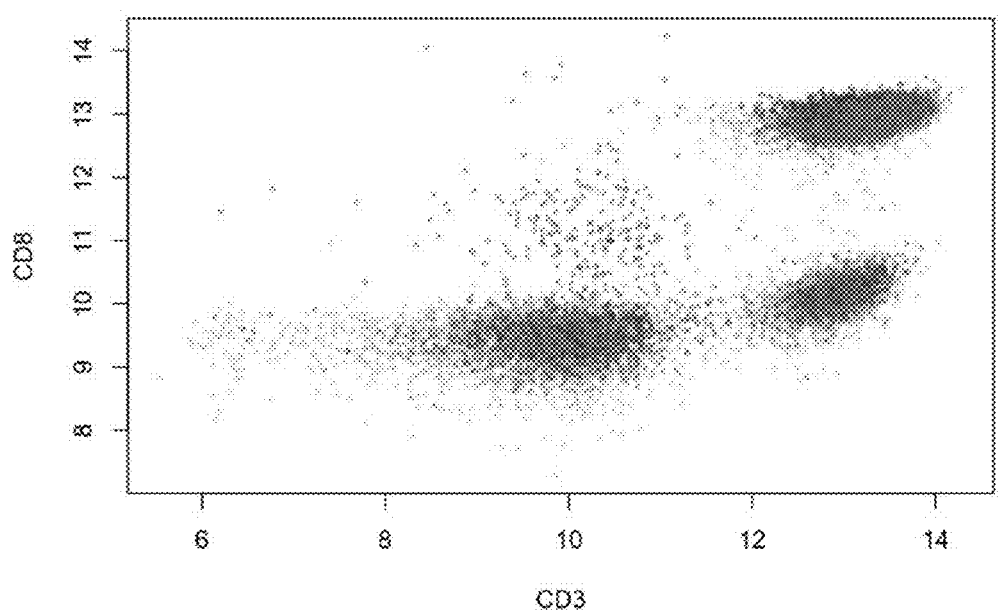
FIG. 18: Re-plotting the framed lymphocytes of FIG. 17 in the channels corresponding to CD3 and CD8

FIG. 18 shows a plot of the framed lymphocytes of FIG. 17 in the channels corresponding to CD3 and CD8. As can be seen the two groups indicated by the colours black and blue do not correspond to distinct populations as defined by the biomarkers CD3 and CD8. Instead they appear to represent a more general, independent property of certain lymphocytes.

Figure 19:
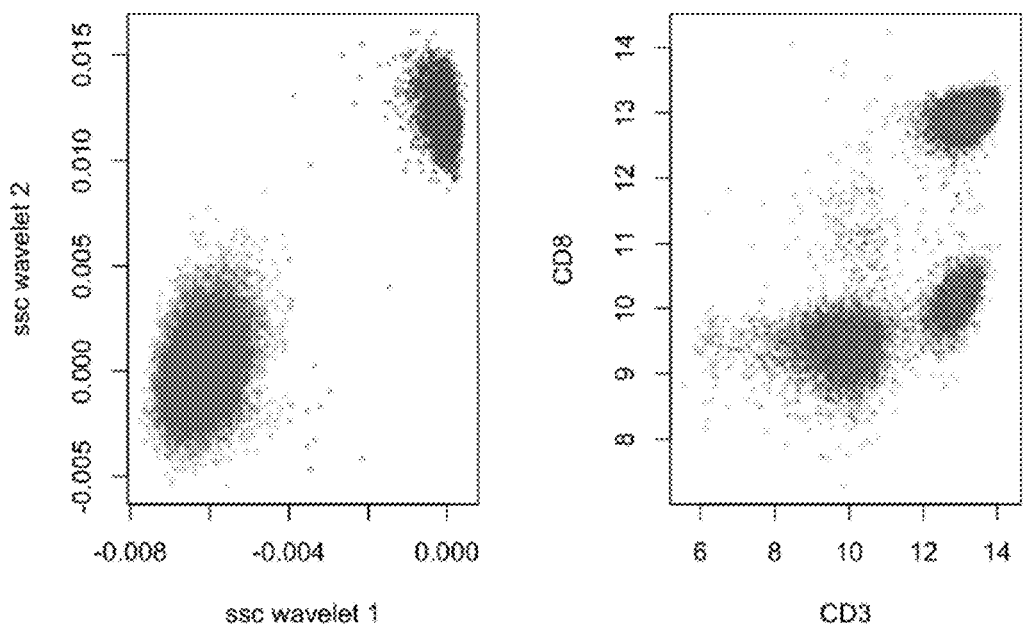
FIG. 19: Comparing the framed lymphocytes in a plot of wavelet coefficients derived by side-scatter and in the channels corresponding to CD3 and CD8

The framed lymphocytes are also used to investigate the wavelet coefficients derived from side scatter. FIG. 19 shows on the left a plot of the side scatter wavelet coefficients. On the right of FIG. 19 the events are plotted in CD3 and CD8 with the colour code that corresponds to the two groups found in the side scatter wavelet coefficient (FIG. 19 left). Also for this analysis the distinct populations found in the side scatter wavelet coefficients do not correspond to populations as defined by the biomarkers CD3 and CD8.

Figure 20:
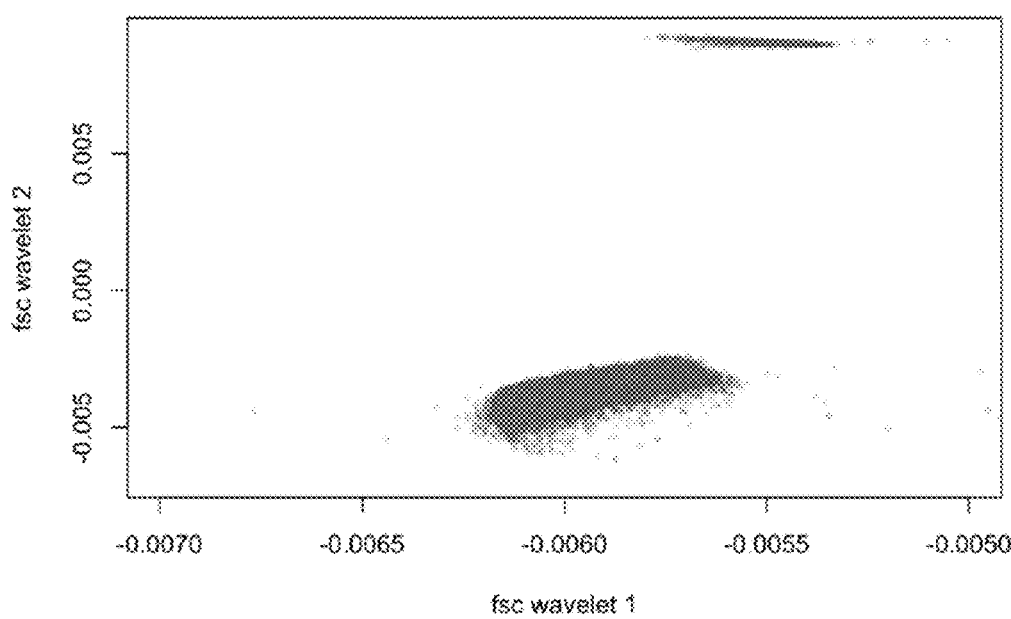
FIG. 20: Re-plotting the framed lymphocytes in a plot of the wavelet coefficients derived by forward scatter with a colour code defined by the side scatter wavelet coefficients

FIG. 20 shows a plot of the forward scatter wavelet coefficients of the framed lymphocytes, wherein the colouring is defined by the two groups identified by the plot of the side scatter wavelet coefficients of FIG. 19. As can be seen from FIG. 20 the populations defined by forward scatter and side scatter coefficients are distinct from each other, and appear therefore to represent different properties of the human PBMCs.

Figure 21:
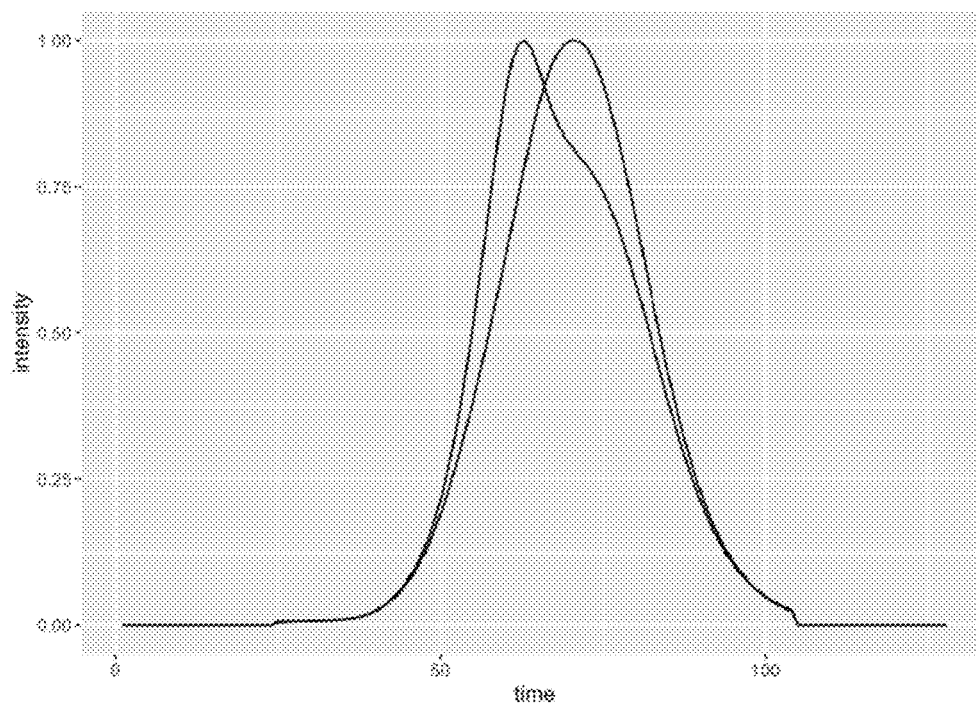
FIG. 21: Plot of the average pulse shape for the two groups in the side scatter wavelet coefficients

In FIG. 21 the average pulse shapes from each of the two groups in the side scatter wavelet coefficients of the framed lymphocytes (see FIG. 19) are plotted.

Figure 22:
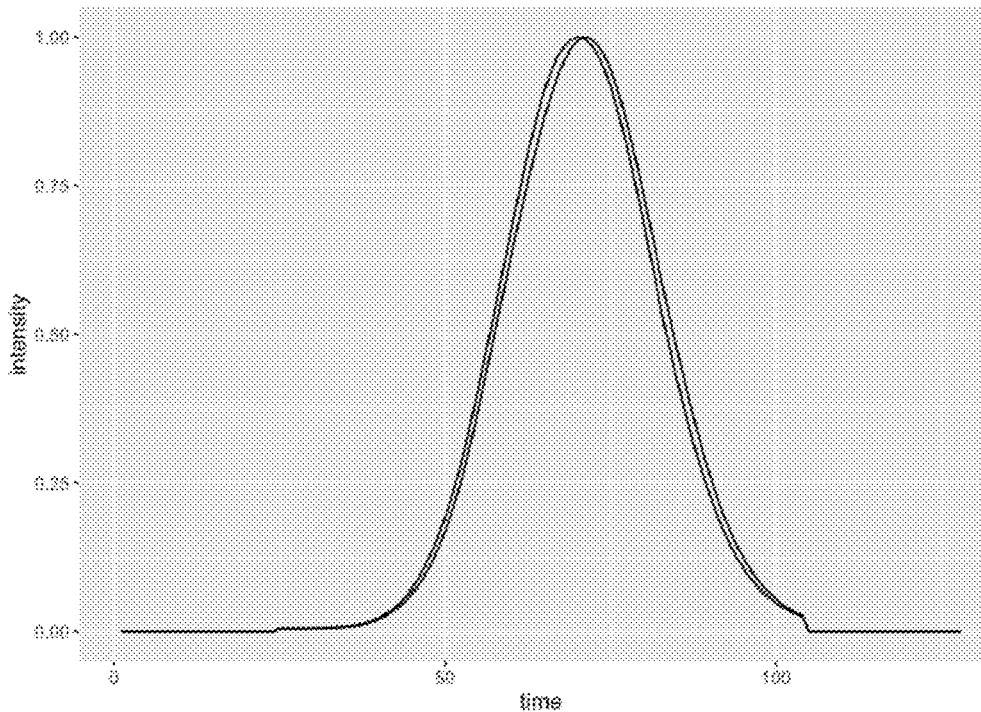
FIG. 22: Plot of the average pulse shape for the two groups in the forward scatter derived wavelet coefficients
Figure 23:
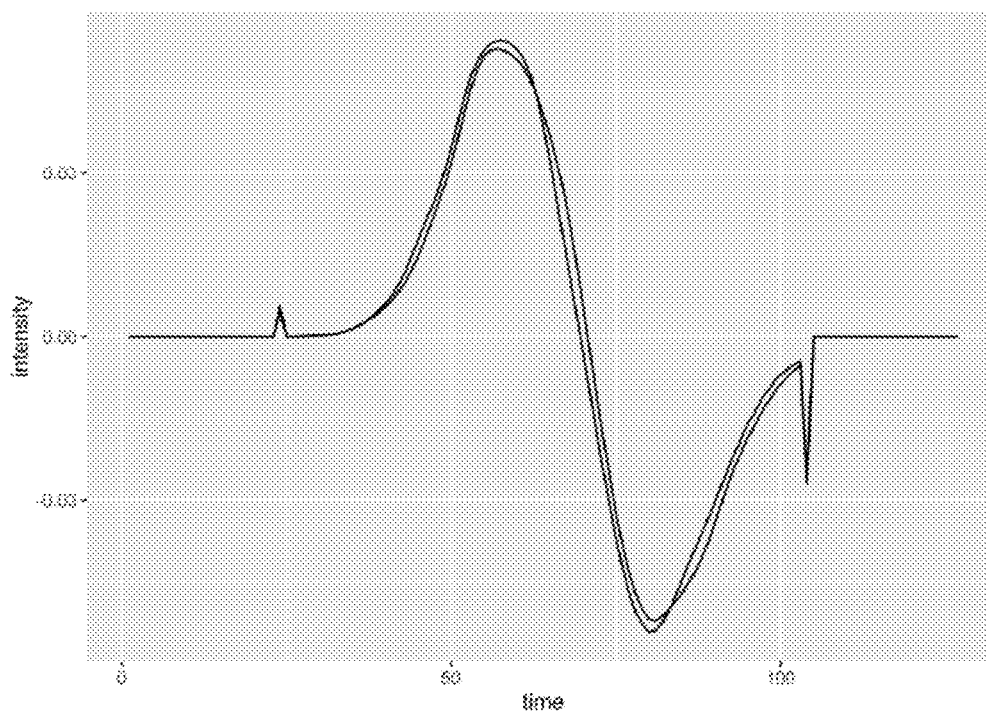
FIG. 23: Plot of the first derivative of the average pulse shapes of FIG. 22

FIG. 22 plots the average pulse shapes from each of the two groups in the forward scatter wavelet coefficients of the framed lymphocytes (see FIG. 20). Since the average pulse shapes are very similar, the first derivative of each of the average pulse shapes is plotted in FIG. 23. The inflection points of the pulse shapes are subtly different, which is difficult to pick by eye. It demonstrates however the potential of using wavelet coefficients for a detecting of such slight differences.

Example 5: Cell Cycle Analysis of Human Colon Cancer Cell Line

Furthermore an analysis of HCT 116 cell lines arrested in G1 and G2/M phase was carried out in order to compare the ability to discriminate between single cells and doublets using a standard analysis and wavelet transformation.

Figure 24:
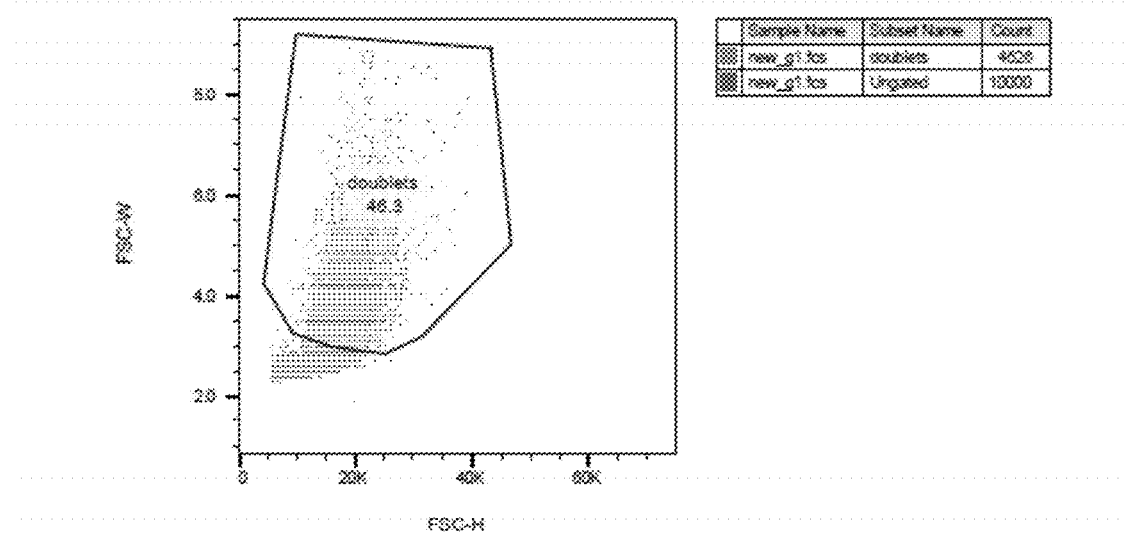
FIG. 24: Plot of standard doublet gate for HCT 116 cells arrested in G1 (top) and G2/M phases (bottom) using list mode parameters height (FSC-H) and width (FSC-W)
Figure 24:
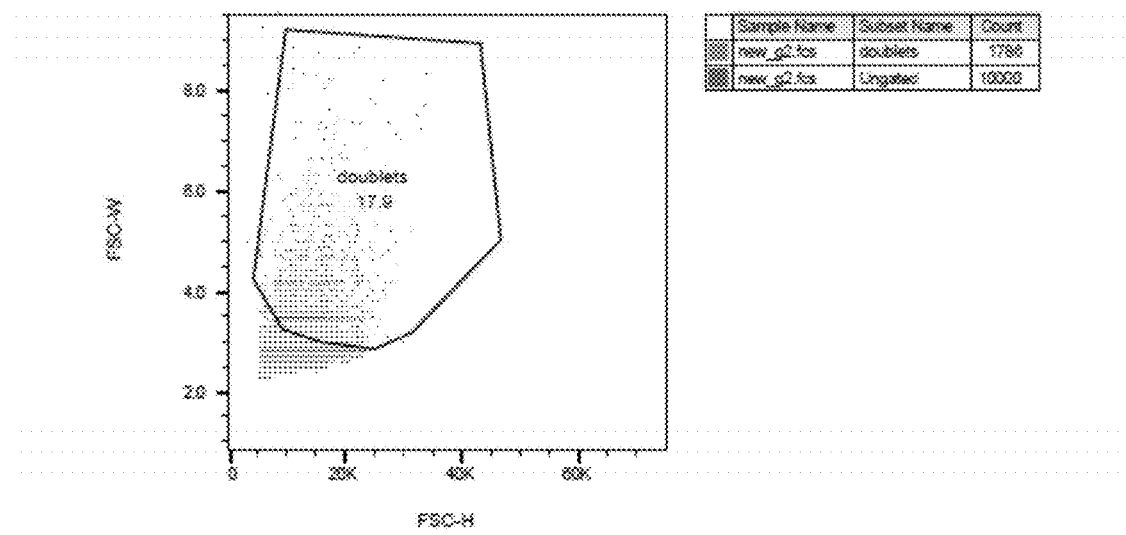

FIG. 24 shows a plot for the forward scatter signal of HCT 116 cells arrested in G1 (top) and G2/M phases (bottom) using standard list mode parameters height (FSC-H) and width (FSC-W). These list mode parameters correspond to the Data File Standard for Flow Cell Cytometry (FCS) (see Spidlen et al. Data File Standard for Flow Cell Cytometry, Version FCS 3.1, Cytometry A. 77(1) (2010))

In the top figure (G1), two populations are visible. The top population exhibits a greater width (FSC-W) than height (FSC-H). In a standard analysis these would commonly assumed to be doublets and omitted from further analysis. A standard doublet gate (black solid line) is introduced to gate the doublets. In the bottom figure (G2), no clear-cut populations can be established. Therefore the standard doublet gate from the top figure is reused.

According to the standard doublet gate 46.3% of the HCT 116 cell arrested in G1 exhibit a doublet shape, while 17.9% of the cells arrested in G2/M exhibit a doublet shape.

Next the results are compared with results obtainable by a wavelet transformation. To this end the waveforms, i.e. the PMT raw data on the pulse shapes are collected at the FCS channel.

As described for Example 1 for each waveform, which corresponds to a triggered event, a discrete wavelet transform (DWT) was run. A DWT function was applied, as used in R, Matlab etc. For reference refer to 'Wavelet Methods in Statistics with R' by Guy Nason (Springer, Use R! Series).

The input for the DWT is a vector of length $2^k$, where k is an integer. The trigger window is preferably padded with zeroes on each end, to become length $2^7$. The output for each cell is a vector of length $2^7$ of wavelet coefficients. To obtain FIG. 25 the DWT coefficients are transformed using a principal component analysis (PCA) and thus the $2^7$ wavelet coefficients are reduced to two coefficients. Here the prcomp function in the statistics software R was used. The axis fsc1 and fsc2 denote two PCA components.

Figure 25:
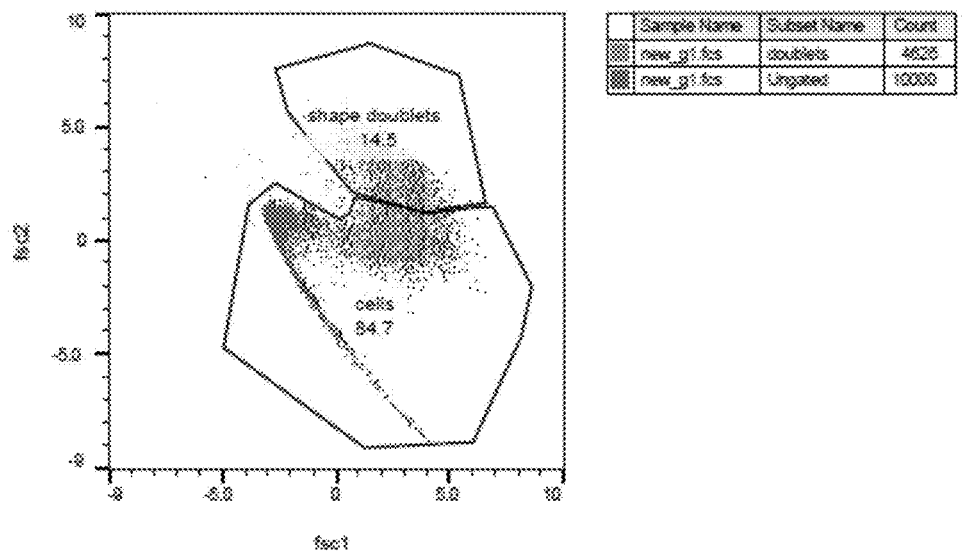
FIG. 25: Plot of the HCT 116 cells of FIG. 24 cells arrested in G1 (top) and G2/M phases (bottom) using PCA on derived wavelet coefficients and definition of a shape double gate
Figure 25:
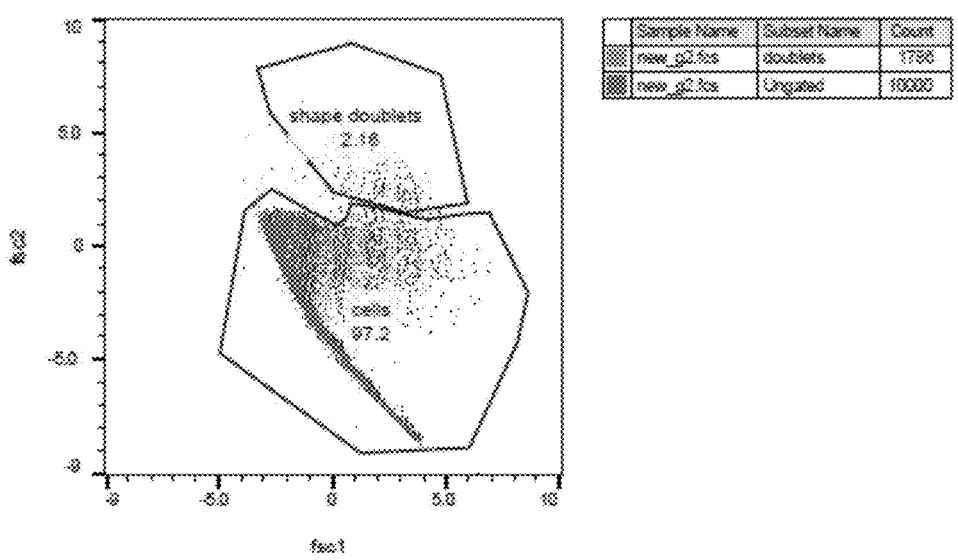

In FIG. 25 the results from the 'standard doublet gate' are displayed in the PCA plot via colour coding, in which blue corresponds to doublets and red to non-doublets. In this view there are more distinct populations, and the 'standard doublet gate' appears too large.

Therefore a new doublet gate was defined (black outline), which will be referred to as the 'shape doublet gate'. We defined the new 'shape doublet gate' by gating on the very distinct and obvious population in the wavelet PCA, and checked where these cells occurred in the standard FSC-H FSC-W plot. According to the shape doublet gate 14.5% of the HCT 116 cells arrested in G1 exhibit a doublet shape, while 2.16% of the cells arrested in G2/M exhibit a doublet shape.

Figure 26:
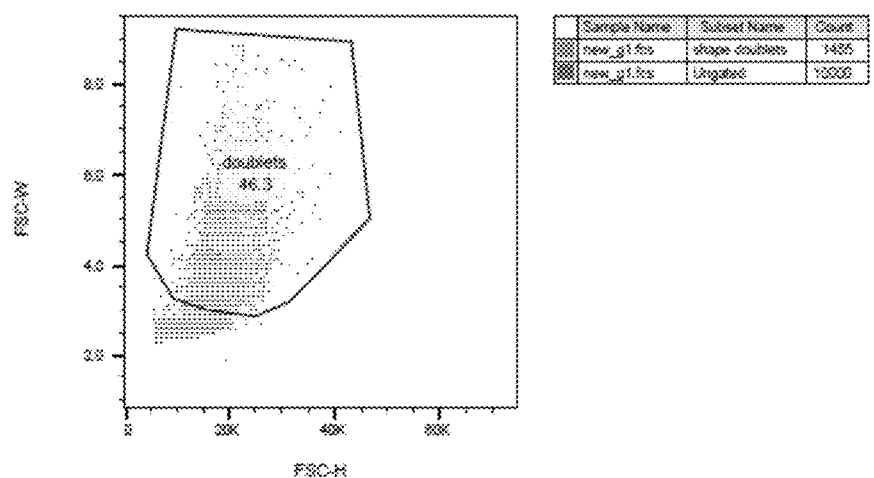
FIG. 26: Re-plotting the HCT 116 cells of FIG. 24 cells arrested in G1 (top) and G2/M phases (bottom) using list mode parameters height (FSC-H) and width (FSC-W) with a colour coding based upon the shape doublet gate as established in FIG. 25.
Figure 26:
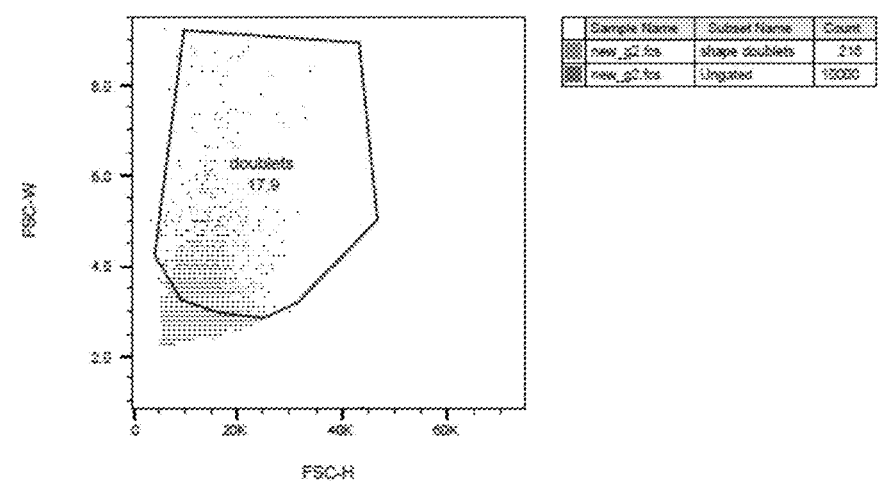

In FIG. 26 the 'shape doublet gate' is displayed via colour coding in the original FSC-H, FSC-W plot (blue indicating doublets according to the 'shape doublet gate' and red indicating ungated events). This is accompanied by a black outline representing the 'standard doublet gate'. As becomes apparent in this illustration, the standard doublet gate is too large. Also the populations of the doublets versus non-doublets as identified by the wavelet transformation do not separate nicely in the standard FSC-H and FCS-W plot, emphasizing that a pure width and height analysis in not sufficient for an accurate separation.

Figure 27:
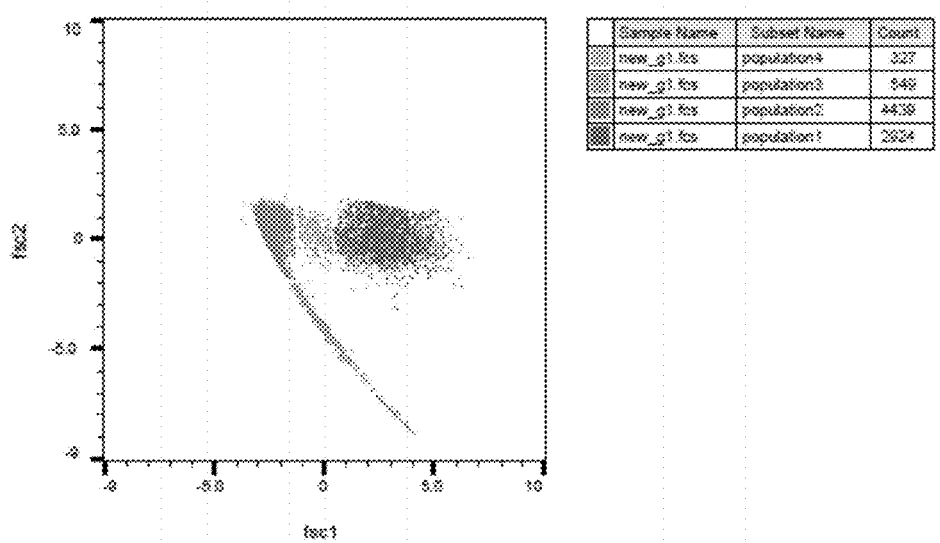
FIG. 27: Plot of a PCA of the wavelet coefficients for the cells gated out using the shape doublet gate revealing four populations of differing autofluorescence
Figure 27:
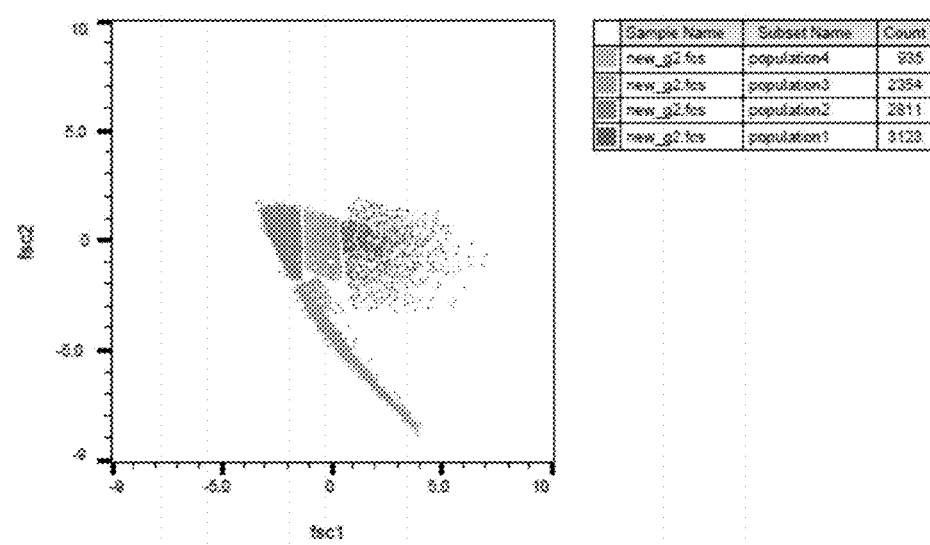

FIG. 27 shows the cells that have been gated out using the shape doublet gate as established from in FIG. 25. In order to visualize the wavelet coefficients a PCA has been performed. Populations were defined by manually drawing clusters in the PCA of the FSC wavelet coefficients, and these results were transferred to the plot of standard fluorescence parameters. Thereby four distinct populations are revealed which reflect differing autofluorescence signals. These four populations are marked by a colour coding. In this case, information about auto fluorescence can be directly derived from the scattered light only, i.e. cell morphology is correlated with autofluorescence. This is another example of unbiased biological discovery.

Figure 28:
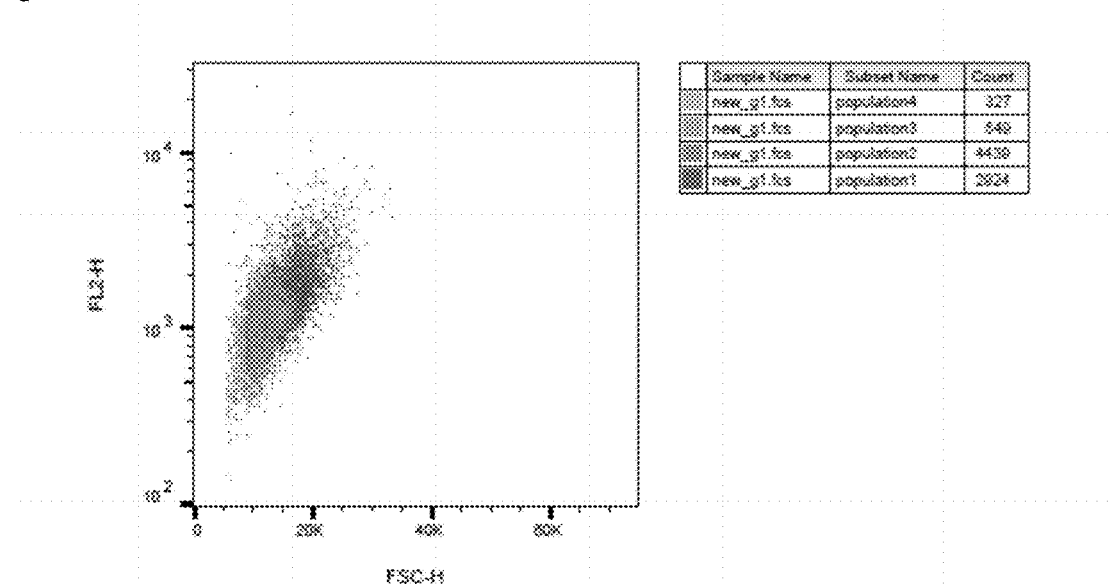
FIG. 28: Re-plotting the cells gated out by the shape doublet gate using the list mode parameters FSC-H and FL2-H with the colour coding of the four populations shown in FIG. 27.
Figure 28:
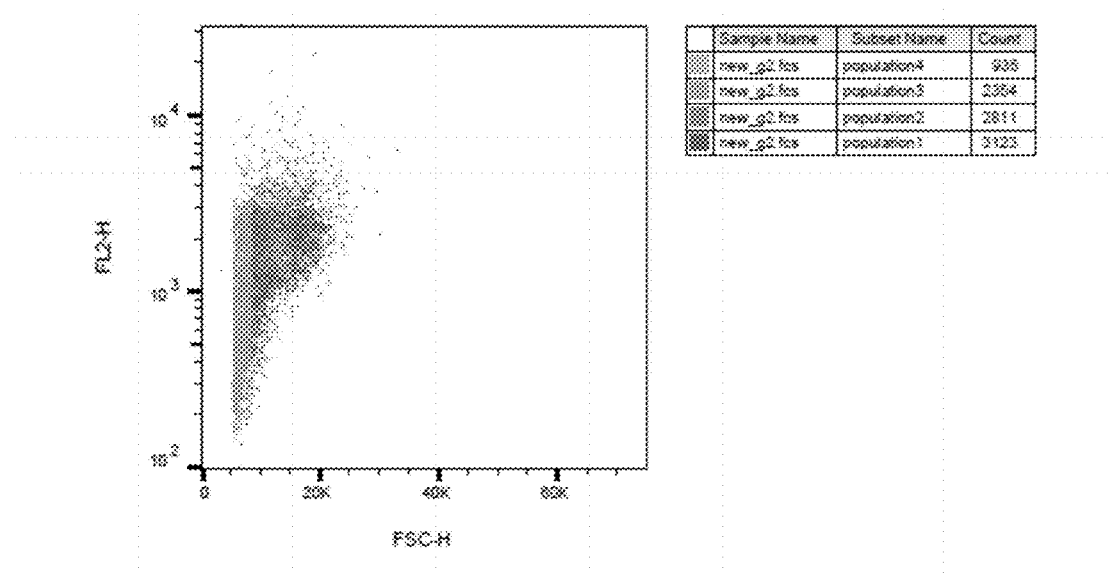

FIG. 28 re-plots the cells gated out by the shape doublet gate using the list mode parameters FSC-H and FL2-H. The colour coding of the populations identified in FIG. 27 is used. These populations have clearly increasing autofluorescence, but in the standard list parameter plots there are no clearly defined populations.

Figure 29:
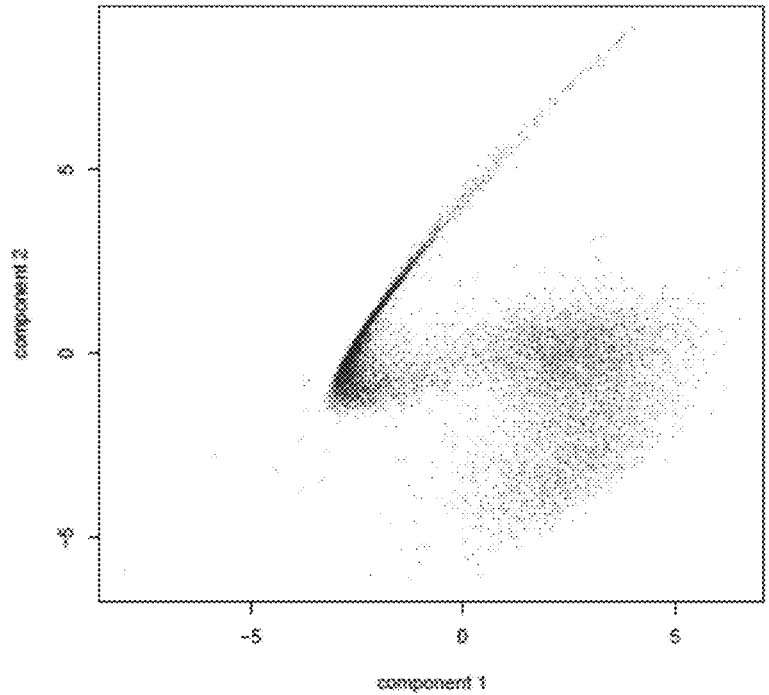
FIG. 29: Alternative visualization in order to illustrate the connection between the PCA of the wavelet coefficients and the shape of the waveforms.
Figure 29:
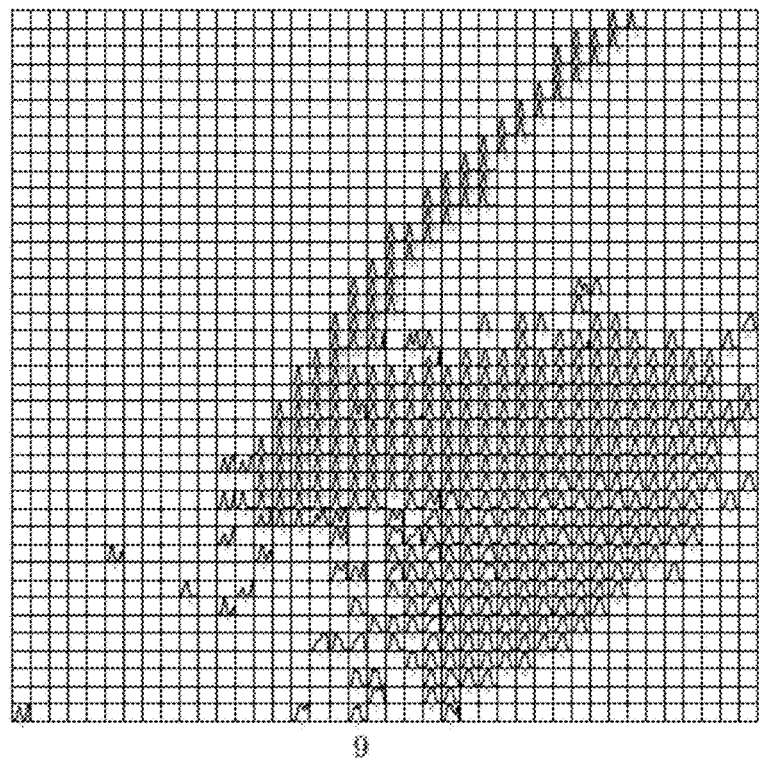

FIG. 29 represents an alternative visualization in order to illustrate the connection between the PCA of the wavelet coefficients and the shape of the waveforms. The top figure is identical to the top FIG. 25, except that the principal component axis have been switched. In the bottom of FIG. 29 at the position of the cells in the PCA plot, the shape of the waveform is displayed as it can be approximated from the wavelet coefficients. This shows that cells designated as doublets in the 'standard doublet gate' are not doublets, according to what is commonly accepted as doublets, but this is invisible in a standard analysis. They appear to be specific cell types of which there is no prior biological knowledge. This further demonstrates the potential of the method for unbiased biological discovery.

Example 6: B Cell Patients

Human B-cells are stained with CD3 and CXCR5, which is a dim staining with no clear cut between positive and negative cells in a standard list mode file. When the raw PMT readout is summarized for the standard list mode file (i.e. FSC-H (height), FSC-W (width), FSC-A (area)), there is no prior decision step to separate waveforms representing a real cell from noise. Therefore, when the detected waveform is smaller than the noise or doesn't exist, the parameters FSC-H, FSC-W and FSC-A are being calculated on a waveform, which does not represent a cell, but noise. This artificially inflates the variance of the negative population. With the standard list mode file, it is also not possible to distinguish between very low autofluorescence signals (waveforms that correspond to real cells) and signals from laser background/electronic noise.

The application of a DWT on the waveforms allows for a separation of the waveforms corresponding to real cells from background noise and makes the positive/negative signal discrimination much more precise.

Figure 30:
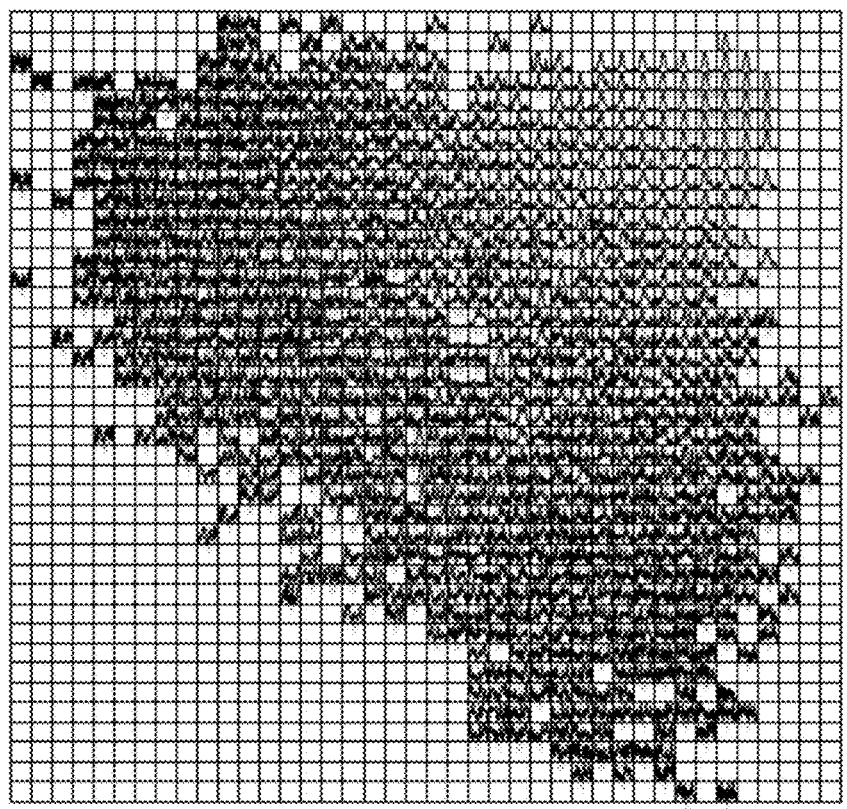
FIG. 30: Visualization of how the DWT PCA relates to the pulse shape continuum using Human B-cells stained with CD3 and CXCR5

FIG. 30 displays the pulse continuum of a fluorescence channel for the Human cells stained with CD3 and CXCR5. A DWT was performed on the waveforms to obtain wavelet coefficients as described about. Subsequently a PCA allows for a visualization of the wavelet coefficients in a reduced dimensional space of the two principal components. Instead to plot a dot at the position of a set wavelet coefficients representing an event in the PCA, the waveform (pulse) is plotted to visualize the shape.

As visible in the top right corner of FIG. 30, there is a smaller population of high quality pulses, corresponding to a positively stained cells and rest of the waveform represent are noise.

Figure 31:
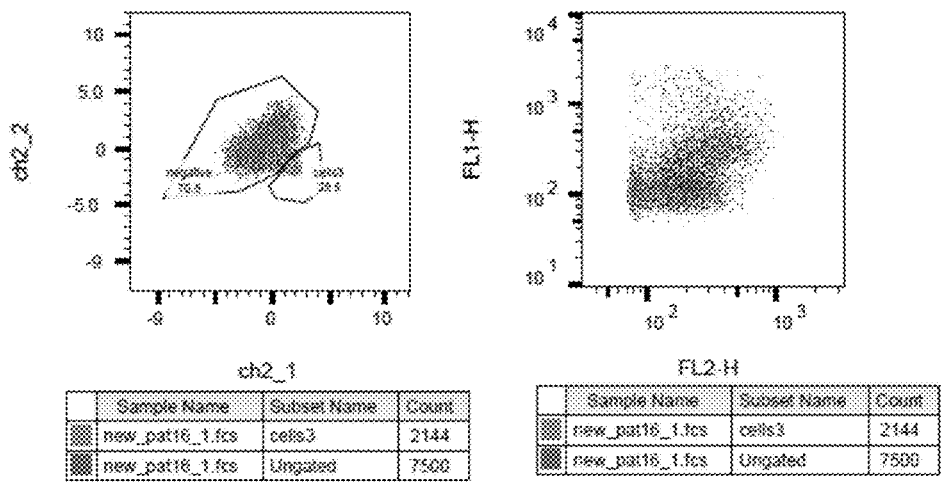
FIG. 31: Positive and negative populations of the B-cells determined by gating on DWT PCA FIG. 32 Illustrates the use of PCA to separate 'ghost events'
Figure 31:
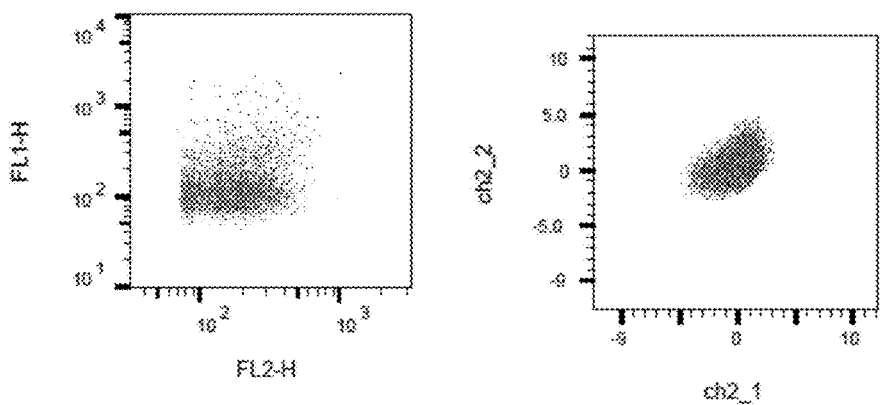

This information can be used to gate out the positive cells (FIG. 31, top left) which is then transferred into a plot using standard list mode parameters (FIG. 31, top right). In FIG. 31, bottom left, it can be seen that there are leftover events that would be typically be labelled as positive in a standard analysis. These cells are backgated into the DWT PCA (FIG. 31, bottom right) and appear in the middle. The procedure can be enhanced by simultaneously measuring a blank sample and performing a DWT Example 7: Eliminating Ghost Events in Forward/Side Scatter It is sometimes possible that FSC will trigger when there is no event. Prior to summarizing an event in a standard list mode by the parameters FSC-H, FSC-W or FSC-A, in standard protocols there is no reliable decision, whether the event actually represents a pulse/waveform of a desired particle. The scatter parameters FSC and SSC are associated with particle size and morphology, but in the process of measuring cells, beads or other desired particles, many undesired events are measured stemming from e.g. cell debris, free fluorochromes etc.

Figure 32:
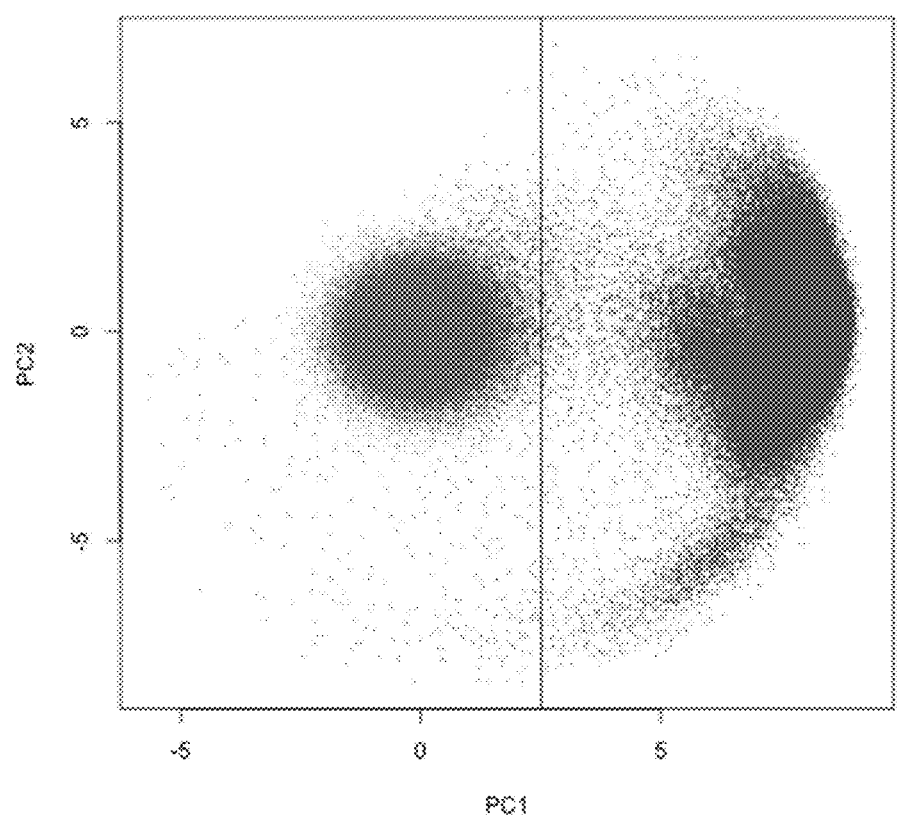

To probe this, a blank sample is measured by connecting the quantiFlash™ device to the FSC channel in order to provide an artificial trigger. In this manner, the pulse shapes in the SSC and fluorescent channels can be captured. The blank sample wavelet coefficients from the fluorescent channels (here six channels) can be combined into one file, as can the coefficients from the real sample. A PCA can be performed on both new datasets together. FIG. 32 displays the results, where blank sample events are blue and real sample events are red. As the blank sample events are not real events, the pulse shapes should be essentially random in all channels, and hence well separated from any real events. By superposing the blank sample with the real sample, it is then possible to judge which events in the real sample correspond to a specific signal. In this example, it is possible to make a very simple gate by drawing a vertical line with ghost events occurring on the left, where the blue points are.

Figure 33:
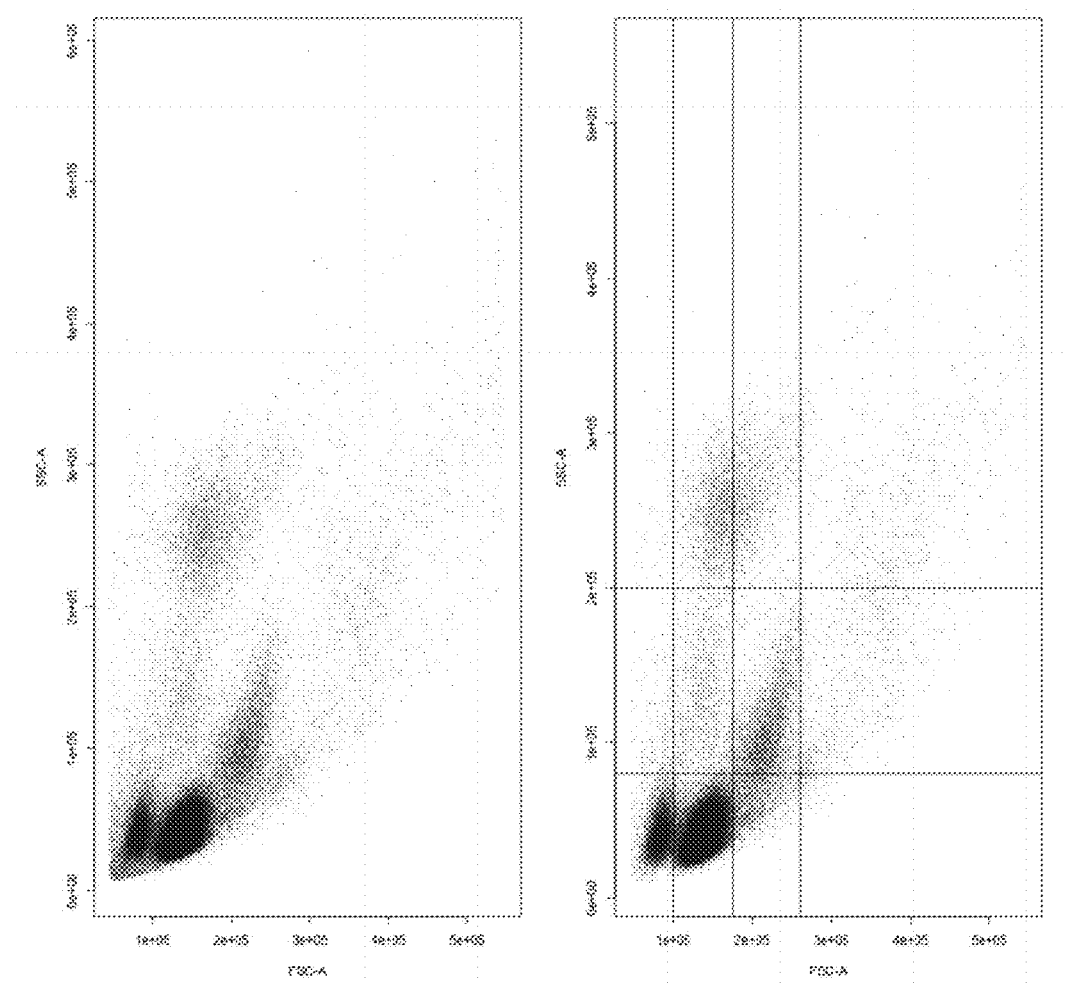
FIG. 33 Illustrates the elimination of ghost events in an FSC-SSC plot
Figure 34:
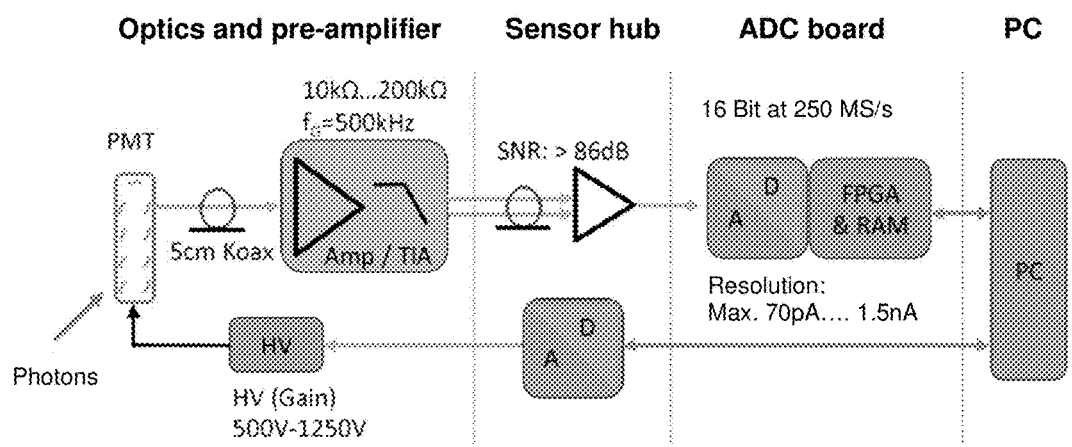
FIG. 34: Schematic representation of the electronics of the flow cytometry system.
Figure 35:
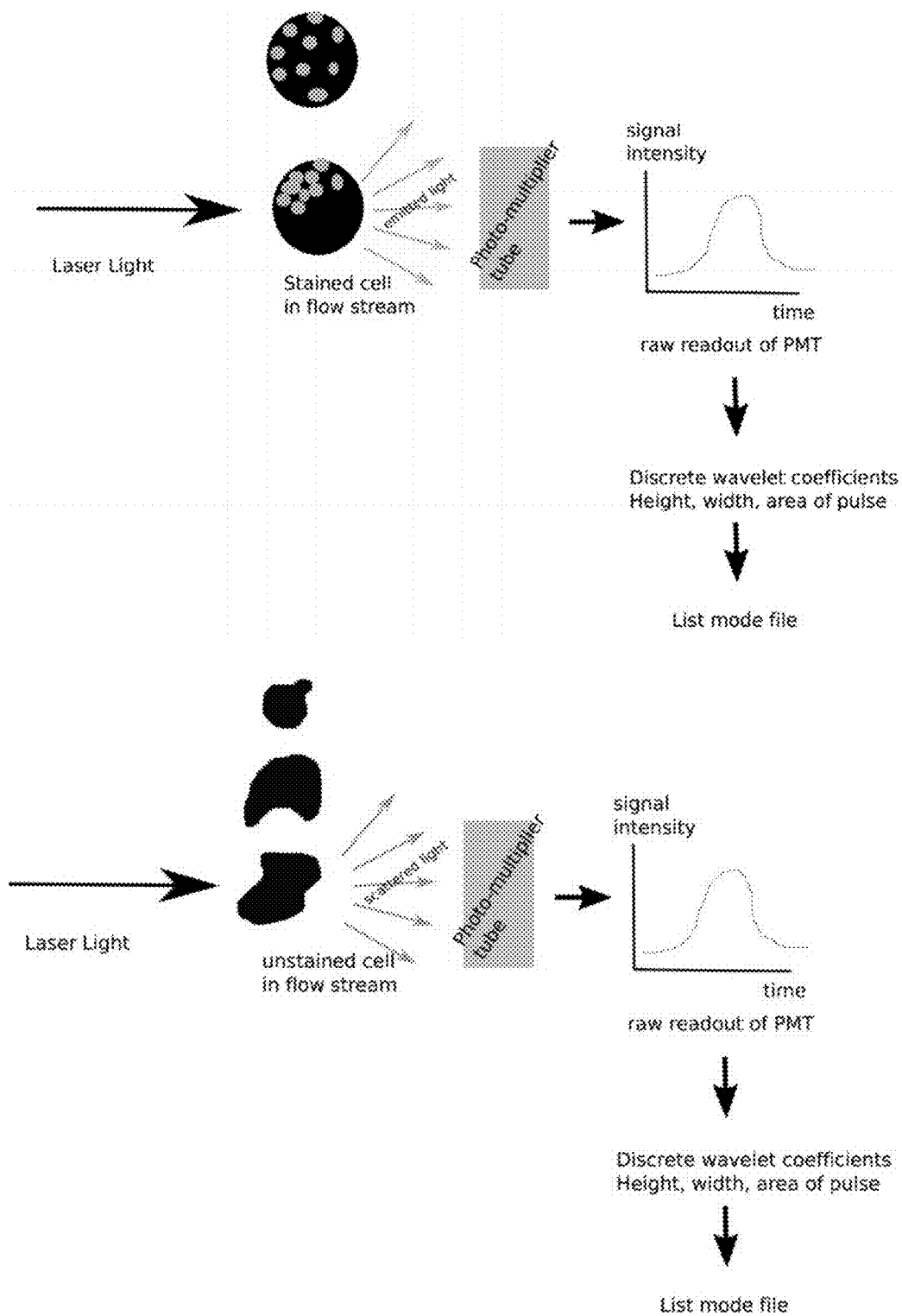
FIG. 35: Schematic representation of the method of the invention.

This gives the possibility to clean out 'ghost events' from FSC/SSC, thus leaving only real particles. These ghost events occur in the region where small particles are also detected. Thus by removing the ghost events, it is possible to improve the detection limit of particles. Experimental results for the ghost extraction are displayed in FIG. 33. In the left figure, all measured events are displayed. In the right figure, the ghost events have been removed, which appear as a low density smear near the origin. This procedure will be advantageous in improving the quality of sorting, by ensuring only real events are sorted. Furthermore, it can also improve the sensitivity of standard flow cytometers, by making it possible to distinguish very dim signals (e.g. auto-fluorescence) from electronic noise.

Example 8: Application of Machine Learning Algorithms for Cell Characterization

In a further example, the potential of a combination of machine learning algorithms to discriminate cells types is demonstrated. To this end a sample of human PBMCs is first gated on FSC/SSC to obtain lymphocytes and then gated into B-cells and other lymphocytes using standard compensated fluorescent parameters. This gating is used to label each cell with one of two labels A or B (B cell or not B cell). One thousand each of events labelled A and B are randomly selected to obtain balanced classes. These events are then randomly split into two groups, labelled training and test. With the training set, an appropriate Support Vector Machine (SVM) with radial kernel is tuned with respect to cost and kernel width parameters. The SVM is constructed using the wavelet coefficients of both FSC and SSC (combined into one single dataset). The parameter combination with the highest classification is chosen. The classification rates for A and B are 75.8% and 78.4% respectively. The SVM is then applied to the test set. The classification rates for A and B are 63.8% and 68.2% respectively.

The standard height/width/area FSC and SSC parameters are not able to separate B cells from other lymphocytes, and fluorescent parameters are necessary. In contrast, the wavelet coefficients demonstrate the possibility of separating B cells from other lymphocytes on the basis of scattered light alone. It is anticipated that further hardware tuning leads to a further improvement in classification rates.

The invention claimed is:

1. A method for characterizing particles using a flow cytometer comprising:
   a. passing of one or more particles in a fluid stream through a light beam of the flow cytometer,
   b. detecting radiated light as one or more particles pass through the light beam,
   c. generating a waveform which is a digital representation of the detected radiated light, and
   d. transforming said waveform by applying one or more basis functions and obtaining one or more coefficients characterizing the waveform, wherein transforming said waveform comprises:
      transforming the waveform by a wavelet transformation using one or more wavelets as the one more basis functions and obtaining one or more wavelet coefficients characterizing the waveform, or
      transforming the waveform by a Fourier transformation using one or more sine functions, one or more cosine functions, or a combination of sine and cosine functions as the one or more basis functions and obtaining one or more Fourier coefficients characterizing the waveform, and
   e. assigning a physical or biological property to the one or more particles based on the one or more wavelet or Fourier coefficients characterizing the waveform.

2. The method according to claim 1, wherein the wavelet transformation is a discrete wavelet transformation, a continuous wavelet transformation, a single level wavelet transformation, a multilevel wavelet transform or a combination thereof.

3. The method according to claim 1, wherein the waveform is corrected for the background level prior to the transformation.

4. The method according to claim 1, wherein the waveform is transformed and a set of one or more coefficients characterizing the waveform are obtained, such that, based upon the one or more coefficients and the basis function, an approximated waveform can be generated.

5. The method according to claim 1, wherein the waveform is generated from the detected radiated light using a processing unit that comprises an analog-to-digital converter (ADC).

6. The method according to claim 1, wherein the waveform is transformed using a processing unit comprising a field programmable gate array (FPGA).

7. The method according to claim 1, wherein the particles are calibration samples with at least one known property and the correlation of the one or more coefficients of the waveform of said calibration samples is calculated to generate a calibration matrix.

8. The method according to claim 1, wherein the coefficients characterizing the waveform are analysed using a principal component analysis.

9. The method according to claim 8, wherein clusters of coefficients are identified in the space of the principle components that indicate a common property of the corresponding particles.

10. The method according to claim 1, wherein the particles are selected from a group comprising cells, vesicles, nuclei, microorganisms, beads, proteins, nucleic acids, pollen, extracellular vesicles or any combination thereof.

11. The method according to claim 1, wherein the particles are cells and the determined property of the cells is or is associated with cell type, localization or distribution of molecules within the cell or on the cell surface, the amount of debris on the cell, structural elements of the cell such as the nucleus or the cytoskeleton, antibody or antibody-fragment binding to the cell, cell morphology or allows for the distinction between single cells or aggregates of multiple cells.

12. A flow cytometry system comprising:
a source for a fluid and particles,
a fluid nozzle configured to generate a fluid stream comprising the particles,
a light source configured to generate a light beam that illuminates the fluid stream comprising the particles,
a detector configured to detect the radiated light of the particles, and
a processing unit configured to generate a waveform based upon the detected radiated light,
wherein the processing unit is configured to transform said waveform by applying one or more basis functions, obtain one or more coefficients characterizing the waveform, and assign a physical or biological property of the one or more particles based on the one or more coefficients,
wherein the processing unit is configured to transform said waveform by a wavelet transformation using one or more wavelets as the one or more basis functions and obtaining one or more wavelet coefficients characterizing the waveform, or
wherein the processing unit is configured to transform said waveform by a Fourier transformation using one or more sine functions, one or more cosine functions, or a combination of sine and cosine functions as the one or more basis functions and obtaining one or more Fourier coefficients characterizing the waveform.

13. The flow cytometry system according to claim 12, wherein the processing unit comprises an ADC and a FPGA.

14. The flow cytometry system according to claim 12, wherein the processing unit is configured to transform the waveform by a wavelet transformation.

15. The flow cytometry system according to claim 14 wherein the processing unit is configured to transform the waveform by a discrete wavelet transformation, a continuous wavelet transformation, a single level wavelet transformation, a multilevel wavelet transform or a combination thereof.

16. The flow cytometry system according to claim 12, wherein the processing unit is configured to transform the waveform by a Fourier transformation.

17. The flow cytometry system according to claim 12, wherein the flow cytometry system comprises a sorter for the particles configured to sort the particles based upon the one or more coefficients characterizing the waveform.

18. The method according to claim 1, wherein the Fourier transform is selected from the group consisting of a discrete Fourier transform, a fast Fourier transform, a short-time Fourier transform and any combination thereof.

* * * * *